(12) United States Patent
Pecina

(10) Patent No.: US 12,704,494 B2
(45) Date of Patent: Aug. 11, 2026

(54) SYSTEM AND METHOD FOR INSPECTING COMPONENTS FABRICATED USING A POWDER METALLURGY PROCESS

(71) Applicant: The Boeing Company, Chicago, IL (US)

(72) Inventor: Joseph A. Pecina, Lynnwood, WA (US)

(73) Assignee: The Boeing Company, Arlington, VA (US)

( * ) Notice: Subject to any disclaimer, the term of this patent is extended or adjusted under 35 U.S.C. 154(b) by 1017 days.

(21) Appl. No.: 17/813,658

(22) Filed: Jul. 20, 2022

(65) Prior Publication Data

US 2024/0027420 A1 Jan. 25, 2024

(51) Int. Cl.

| | |
|---|---|
| ***G01N 33/2045*** | (2019.01) |
| ***B22F 3/22*** | (2006.01) |
| ***B22F 3/24*** | (2006.01) |
| ***G01N 3/60*** | (2006.01) |

(52) U.S. Cl.

CPC ......... *G01N 33/2045* (2019.01); *B22F 3/225* (2013.01); *B22F 3/24* (2013.01); *G01N 3/60* (2013.01); *B22F 2003/248* (2013.01)

(58) Field of Classification Search

CPC ...... G01N 33/2045; G01N 3/60; B22F 3/225; B22F 3/24; B22F 2003/248

See application file for complete search history.

(56) References Cited

U.S. PATENT DOCUMENTS

| | | | | |
|---|---|---|---|---|
| 5,328,500 | A | 7/1994 | Beltz et al. | |
| 5,445,688 | A | 8/1995 | Gigliotti, Jr. et al. | |
| 7,698,944 | B2 * | 4/2010 | Takada | G01N 29/041 73/644 |

(Continued)

FOREIGN PATENT DOCUMENTS

| | | | | |
|---|---|---|---|---|
| JP | 2005164355 | * | 6/2005 | G01N 3/00 |
| WO | WO 01/92868 | | 12/2001 | |

OTHER PUBLICATIONS

Liu et al., Deformation behavior and strength evolution of MIM compacts during thermal debinding, State Key Laboratory of Powder Metallurgy, 2007 (Year: 2007).*

(Continued)

*Primary Examiner* — Catherine T. Rastovski
*Assistant Examiner* — Sharah Zaab
(74) *Attorney, Agent, or Firm* — Walters & Wasylyna LLC

(57) ABSTRACT

A nondestructive inspection method includes steps of: (1) forming a first inspection standard using a metal injection molding process; (2) forming a second inspection standard using the metal injection molding process; and (3) creating a reference library that includes the first and the second inspection standards. The first inspection standard includes a first crack, induced by at least one of a thermal shock and a thermal stress. The second inspection standard includes a second crack, induced by at least one of the thermal shock and the thermal stress. At least one of the thermal shock and the thermal stress introduced during a sintering operation for the first inspection standard is different than at least one of the thermal shock and the thermal stress introduced during the sintering operation for the second inspection standard. The first crack and the second crack are different.

20 Claims, 13 Drawing Sheets

(56) References Cited

U.S. PATENT DOCUMENTS

| | | | | |
|---|---|---|---|---|
| 2002/0043364 | A1* | 4/2002 | Suzuki | H01L 23/3733 165/185 |
| 2006/0201280 | A1* | 9/2006 | Hwang | B22F 3/225 75/246 |
| 2009/0177417 | A1* | 7/2009 | Yonemura | G06F 30/15 702/42 |
| 2011/0253926 | A1* | 10/2011 | Hayashi | G11B 5/851 204/192.15 |
| 2014/0184786 | A1* | 7/2014 | Georgeson | G01M 99/00 348/128 |

OTHER PUBLICATIONS

Deformation behavior and strength evolution of MIM compacts during thermal debinding (Year: 2007).*

* cited by examiner

SYSTEM AND METHOD FOR INSPECTING COMPONENTS FABRICATED USING A POWDER METALLURGY PROCESS

FIELD

The present disclosure relates generally to non-destructive inspection and, more particularly, to a system and method for non-destructive inspection of metallic components fabricated using a powder metallurgy process.

BACKGROUND

Powder metallurgy manufacturing, also known as powder metal manufacturing, refers to any one of a variety of manufacturing processes in which parts, also referred to as powder metal parts, are made from metal powders. The powder metal manufacturing process enables components to be made with complex geometry, while decreasing manufacturing costs. Powder metal manufacturing also enables powder metal components to be manufactured having a net or near net shape, which reduces material costs and waste.

Nondestructive inspection, also referred to as nondestructive testing, can be utilized to inspect and/or test a part without destroying, damaging, or otherwise impacting the integrity of the inspected part. As such, nondestructive inspection may be valuable for testing manufactured parts after fabrication of the part. For example, nondestructive inspection can be utilized to detect and/or to quantify defects in manufactured parts, thereby permitting validation of a manufacturing process and/or ensuring that any defects in the manufactured part, if present, are within acceptable tolerances.

A variety of nondestructive testing methodologies exist. However, there is a lack of nondestructive testing methodologies that are capable of testing powder metal parts in a manner that is economically efficient. Accordingly, those skilled in the art continue with research and development efforts in the field of nondestructive testing of powder-metallurgy produced components.

SUMMARY

Disclosed are examples of a method for non-destructive testing and a system for non-destructive testing. The following is a non-exhaustive list of examples, which may or may not be claimed, of the subject matter according to the present disclosure.

In an example, the disclosed method includes steps of: (1) forming a first inspection standard using a metal injection molding process; (2) forming a second inspection standard using the metal injection molding process; and (3) creating a reference library that includes the first inspection standard and the second inspection standard. The first inspection standard includes a first crack that is induced by introducing at least one of a thermal shock and a thermal stress during a sintering operation of the metal injection molding process. The second inspection standard includes a second crack that is induced by introducing at least one of the thermal shock and the thermal stress during the sintering operation of the metal injection molding process. At least one of the thermal shock and the thermal stress introduced during the sintering operation for the first inspection standard is different than at least one of the thermal shock and the thermal stress introduced during the sintering operation for the second inspection standard. The first crack and the second crack are different.

In another example, the disclosed method includes steps of: (1) forming a plurality of inspection standards using a metal injection molding process; (2) during the metal injection molding process, introducing at least one of a thermal shock and a thermal stress during a sintering operation of the metal injection molding process to induce a crack in each one of the inspection standards; (3) performing a first nondestructive inspection operation on each one of the inspection standards to determine a crack-property of the crack of each one of the inspection standards; (4) selecting a first one of the inspection standards in which the crack-property of the crack is below a threshold crack-property; and (5) selecting a second one of the inspection standards in which the crack-property of the crack is above the threshold crack-property.

In an example, the disclosed system includes a reference library. The reference library includes at least a first inspection standard and a second inspection standard formed by a metal injection molding process. The first inspection standard includes a first crack that is induced by introducing at least one of a thermal shock and a thermal stress during a sintering operation of the metal injection molding process. The second inspection standard includes a second crack that is induced by introducing at least one of the thermal shock and the thermal stress during the sintering operation of the metal injection molding process. The first crack includes a first crack-property that is below a threshold crack-property. The second crack includes a second crack-property that is above the threshold crack-property. The system also includes a first nondestructive inspection device. The first nondestructive inspection device is configured to inspect the first inspection standard and the second inspection standard. The first nondestructive inspection device is configured to qualitatively verify that the first crack-property is below the threshold crack-property and that the second crack-property is above the threshold crack-property. The system further includes a second nondestructive inspection device. The second nondestructive inspection device is configured to inspect the first inspection standard and the second inspection standard. The second nondestructive inspection device is configured to produce a first reference-response associated with the first crack-property of the first inspection standard. The second nondestructive inspection device is configured to produce a second reference-response associated with the second crack-property of the second inspection standard. The system additionally includes a computing device 154. The computing device 154 is configured to store the first reference-response and the second reference-response.

Other examples of the disclosed system and method will become apparent from the following detailed description, the accompanying drawings, and the appended claims.

DETAILED DESCRIPTION

Figure 1:
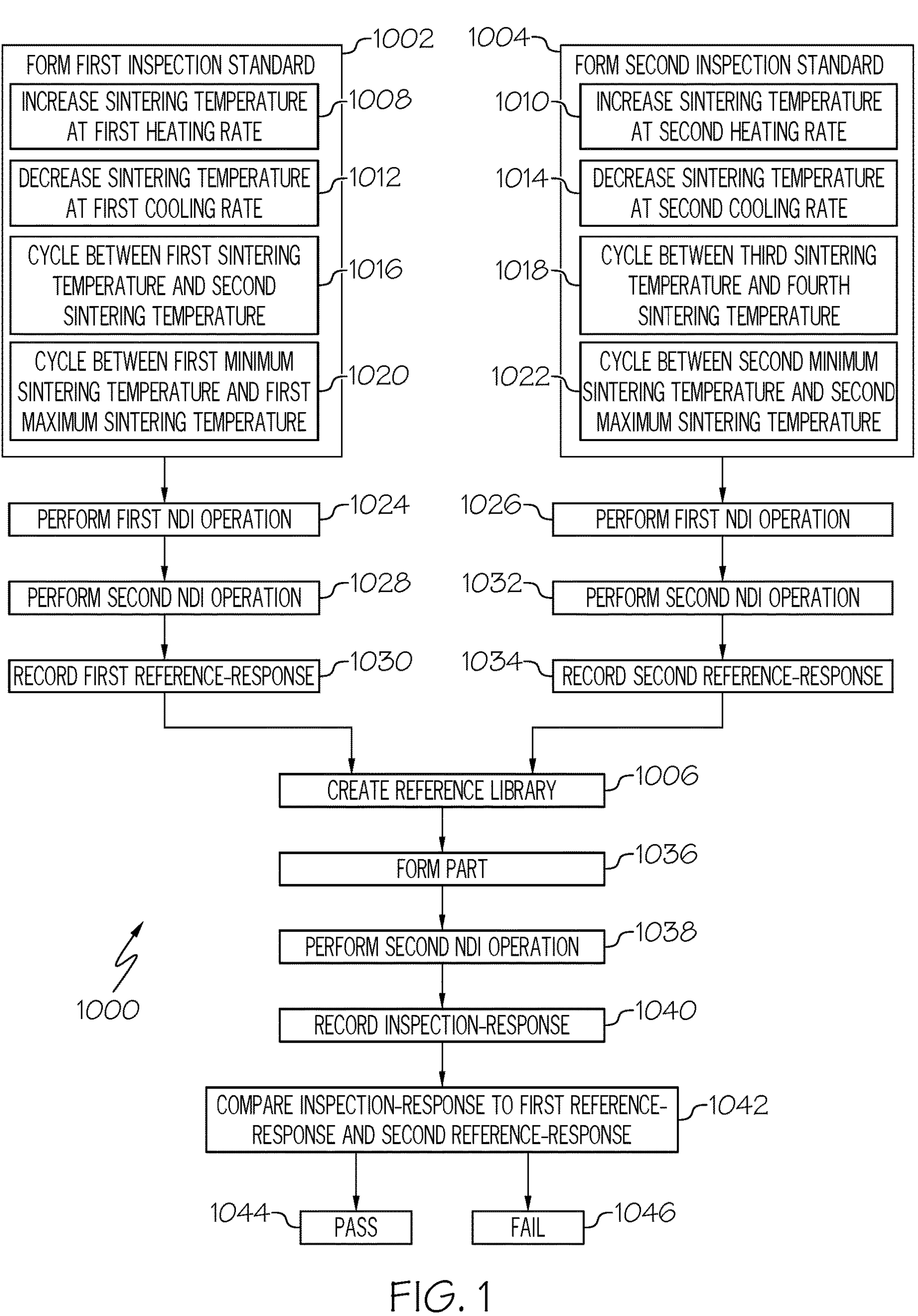
FIG. 1 is a flow diagram of an example of a method for nondestructive testing.
Figure 2:
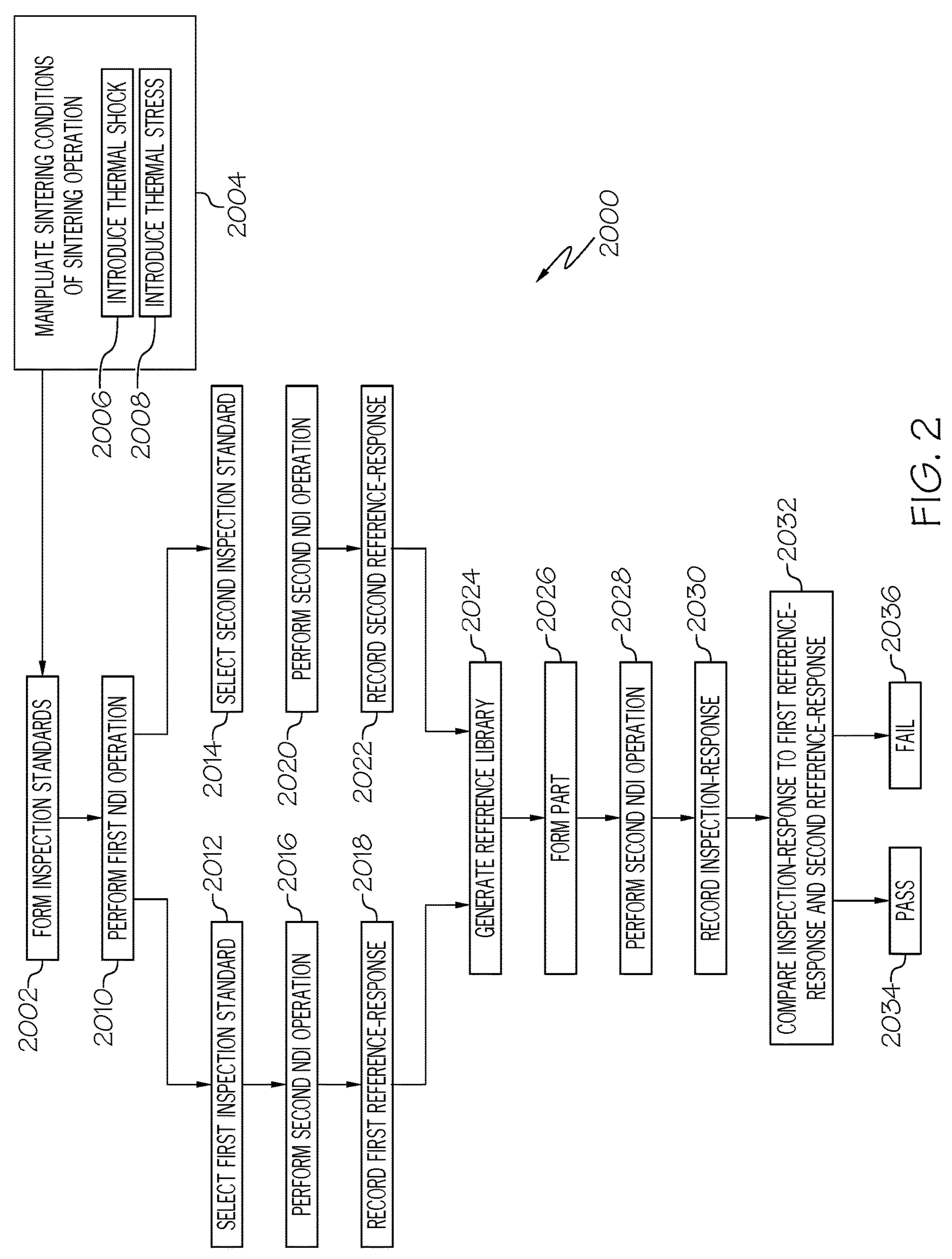
FIG. 2 is a flow diagram of an example of the method for nondestructive testing.
Figure 3:
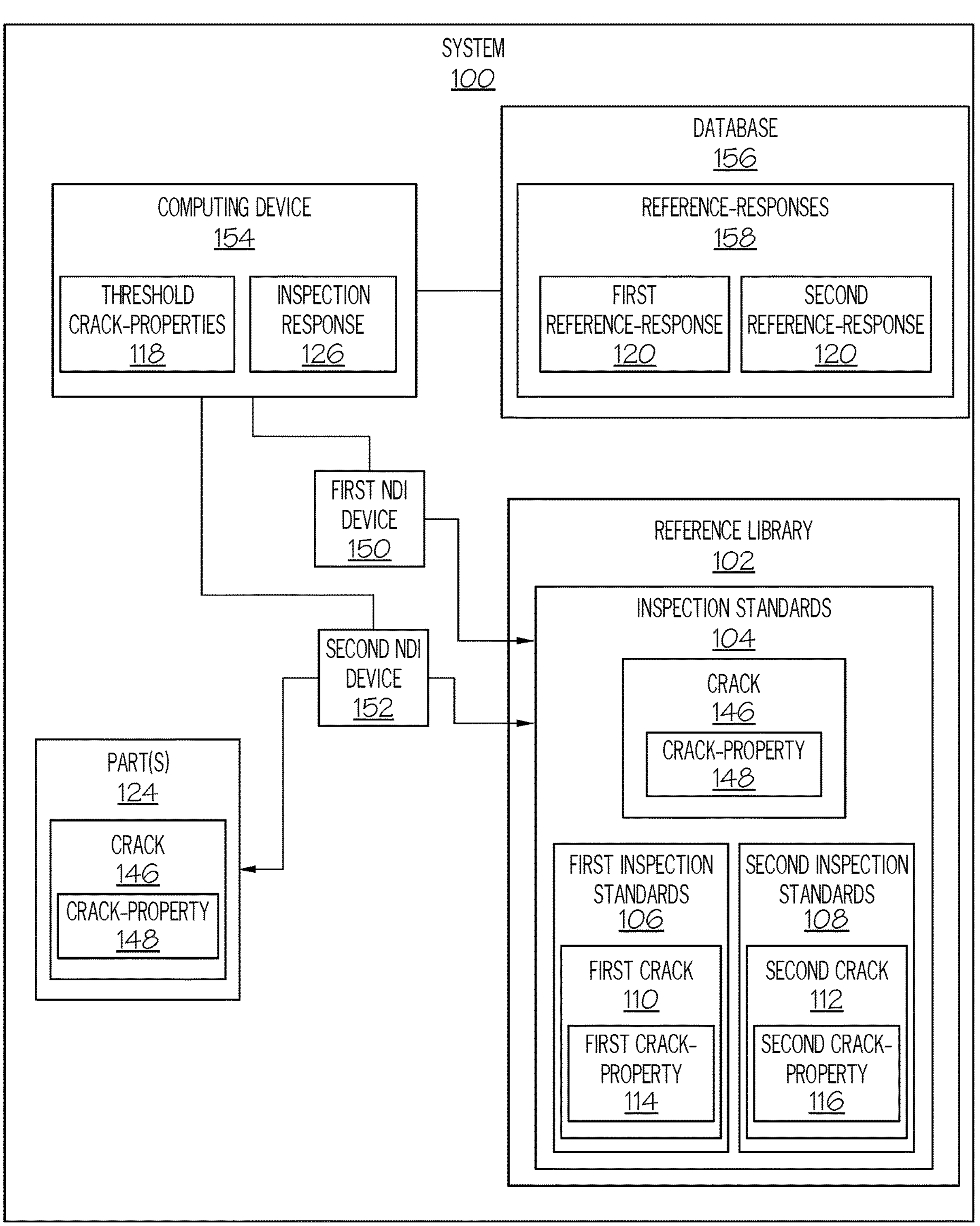
FIG. 3 is a block diagram of an example of a system for nondestructive testing.

Referring generally to FIGS. 1-3, the present disclosure is directed to methods and systems for nondestructive testing (NDT), also referred to as nondestructive inspection (NDI), of powder metal parts. As used herein, a powder metal part refers to a component, object, article, or other structure that is manufactured or otherwise fabricated using a powder metallurgy process.

The present disclosure recognizes that results of nondestructive testing typically need to be correlated with either findings from a destructive test or to a test standard fabricated from similar materials of construction. However, correlating NDI results to results from a destructive test is not practical due to damage or alteration to the manufactured powder metal part. Additionally, nondestructive inspection standards for testing internal cracks in consolidated powder metal parts do not exist. Further, effective methods for creation of nondestructive inspection standards for correlating NDI results has yet to be established for powder metal parts. Moreover, certain visual nondestructive testing methodologies, which do not require correlation with results from destructive testing or a test standard, are prohibitively expensive for use on a mass scale.

Accordingly, certain nondestructive testing methodologies (e.g., non-visual nondestructive testing methodologies) may have limited application for detecting certain properties in powder metal parts, such as internal cracking. The methods and systems disclosed herein provide nondestructive inspection standards, which can be used to assess or qualify results from nondestructive inspection of parts (e.g., manufactured powder metal parts). As will be described herein, the inspection standards include cracks having known crack-properties (e.g., types, dimensions, number, etc.). The inspection standards facilitate qualification of manufactured powder metal parts via comparison between upper and lower limits of a predetermined threshold. The inspection standards also facilitate validation of a nondestructive inspection operation.

Figure 6:
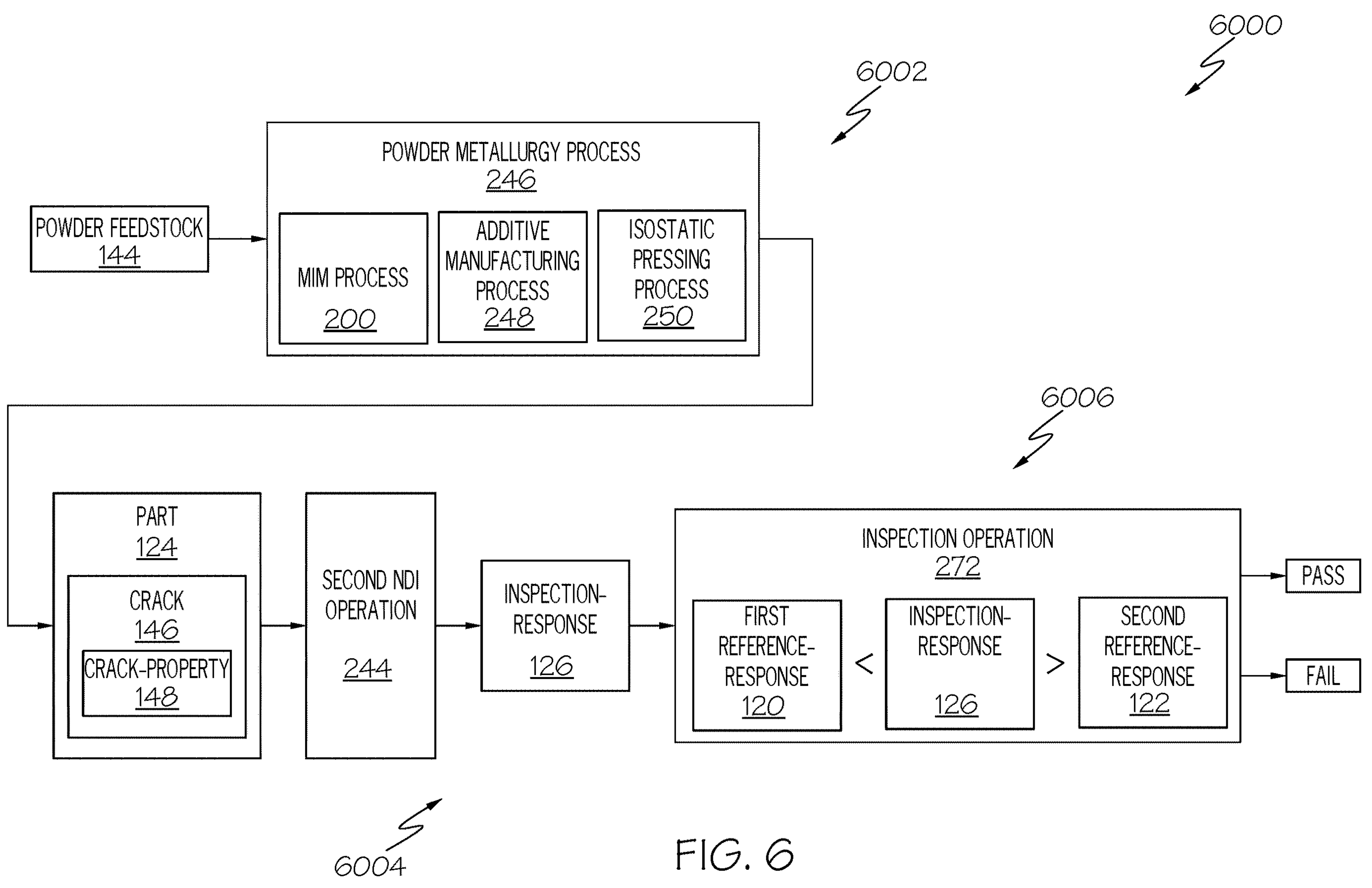
FIG. 6 is a block diagram of an example of an inspection process.

Referring now to FIG. 1, which illustrates an example of a method 1000. The method 1000 is an example of the disclosed methods for nondestructive inspecting of parts 124 (e.g., as shown in FIG. 3). Throughout the present disclosure, the part 124 refers to a powder metal part made using any one of various powder metallurgy processes 246 (e.g., as shown in FIG. 6).

Implementations of the method 1000 provide for creation of nondestructive inspection standards 104 that can be used as references to quantify or validate results of nondestructive inspection of the part 124. Creation of the inspection standards 104 also enable selection and validation of different non-destructive inspection methodologies, which can be used to nondestructively inspect the part 124.

In one or more examples, the method 1000 includes a step of (block 1002) forming a first inspection standard 106 (e.g., as shown in FIG. 3). The first inspection standard 106 is formed (e.g., manufactured, fabricated, or produced) using a metal injection molding process 200 (e.g., shown in FIGS. 4 and 5).

Figure 4A:
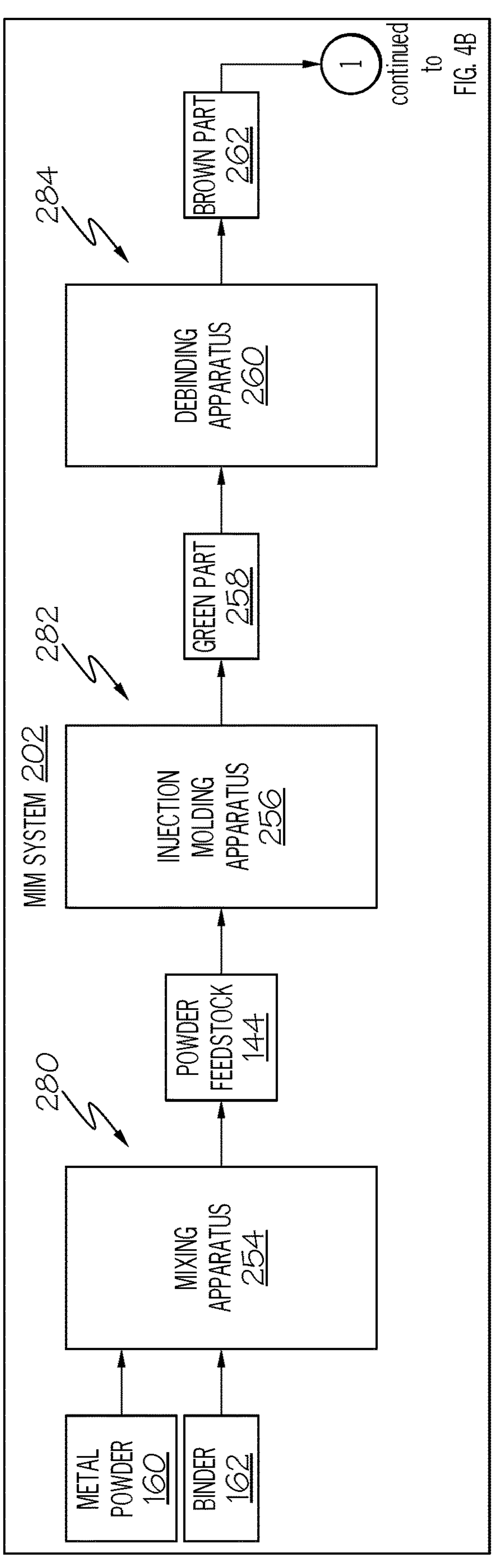
FIGS. 4A, 4B, and 4C, collectively, are a block diagram of an example of metal injection molding process.
Figure 4B:
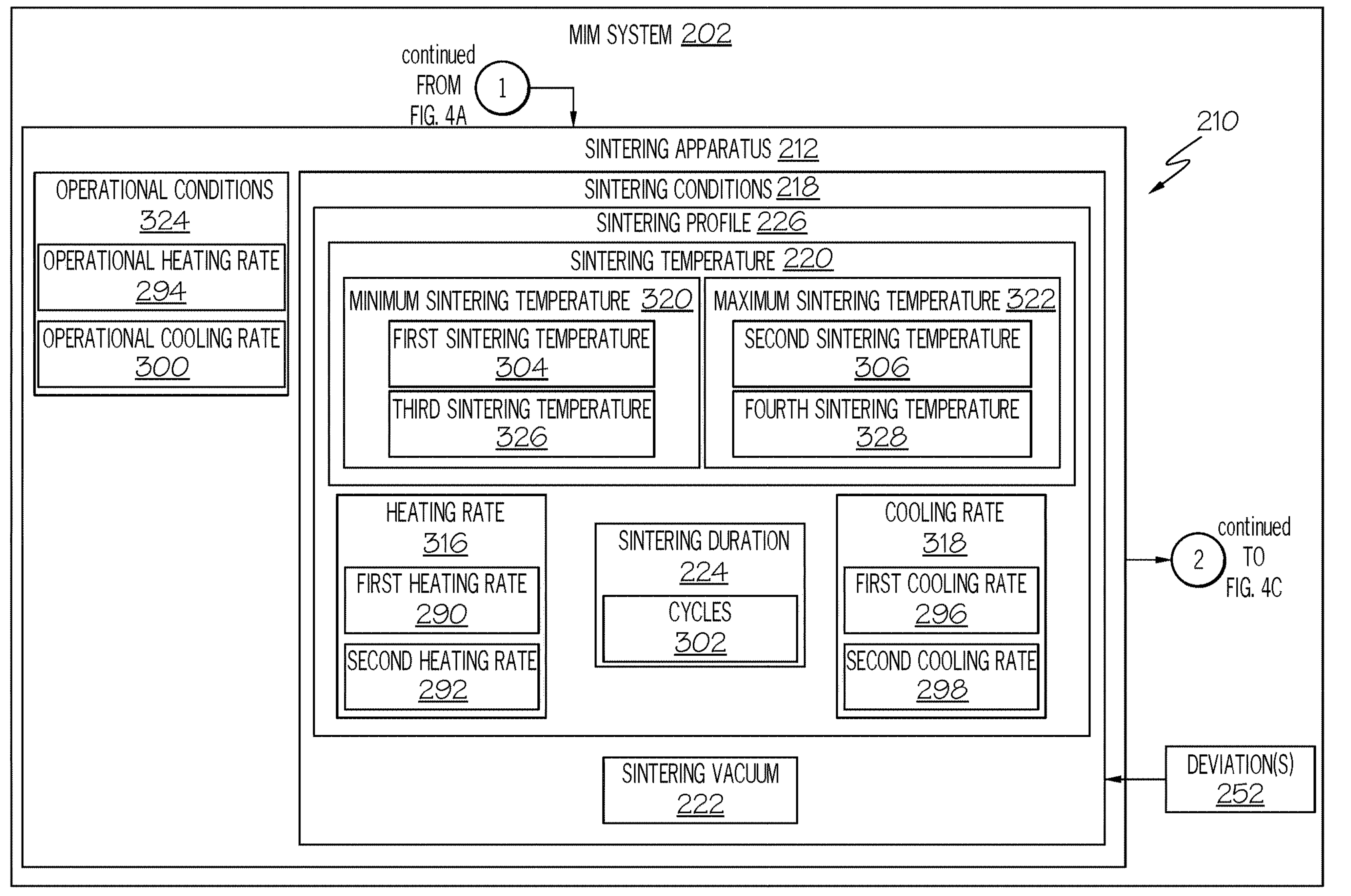
Figure 4C:
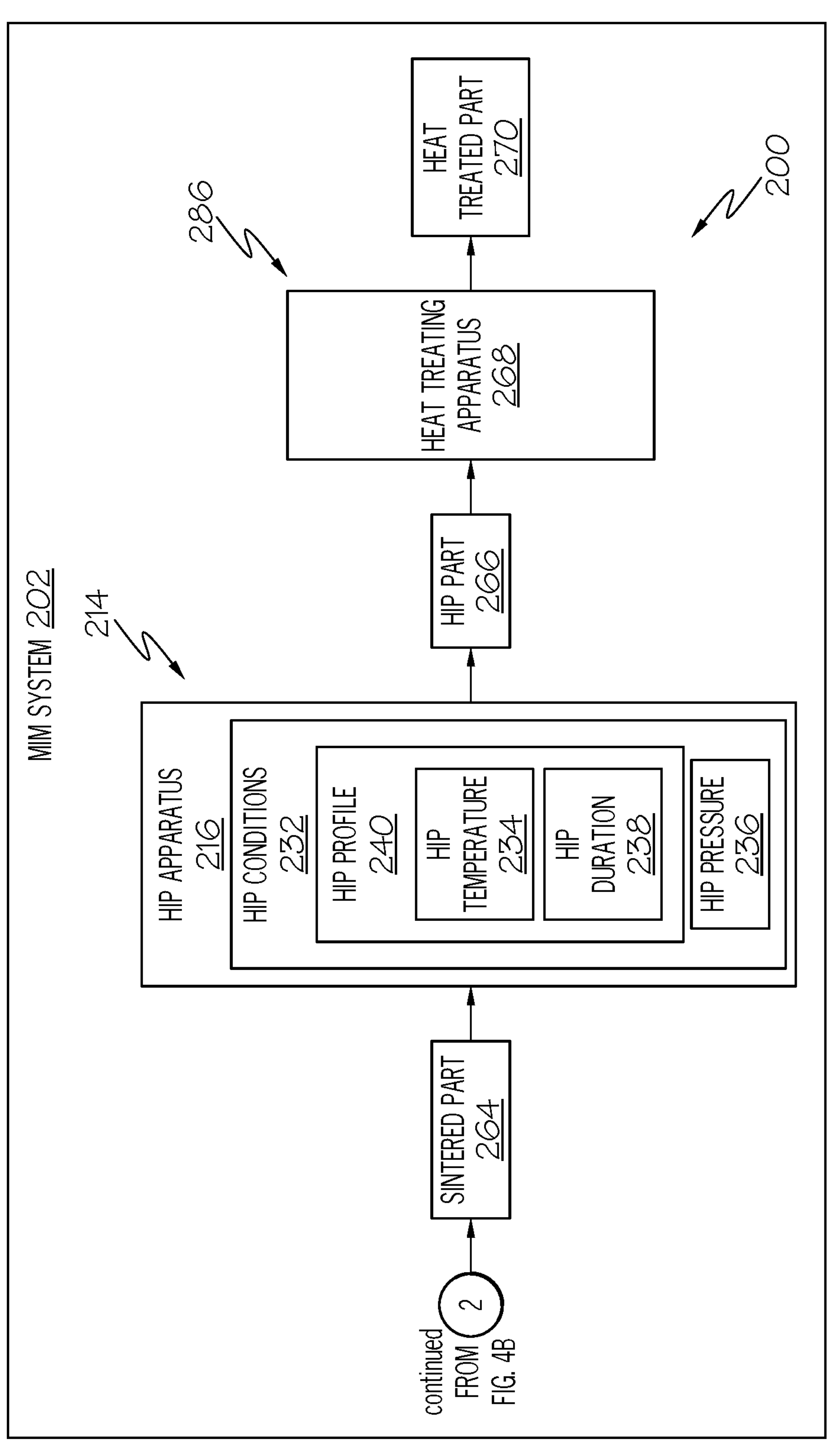
Figure 5:
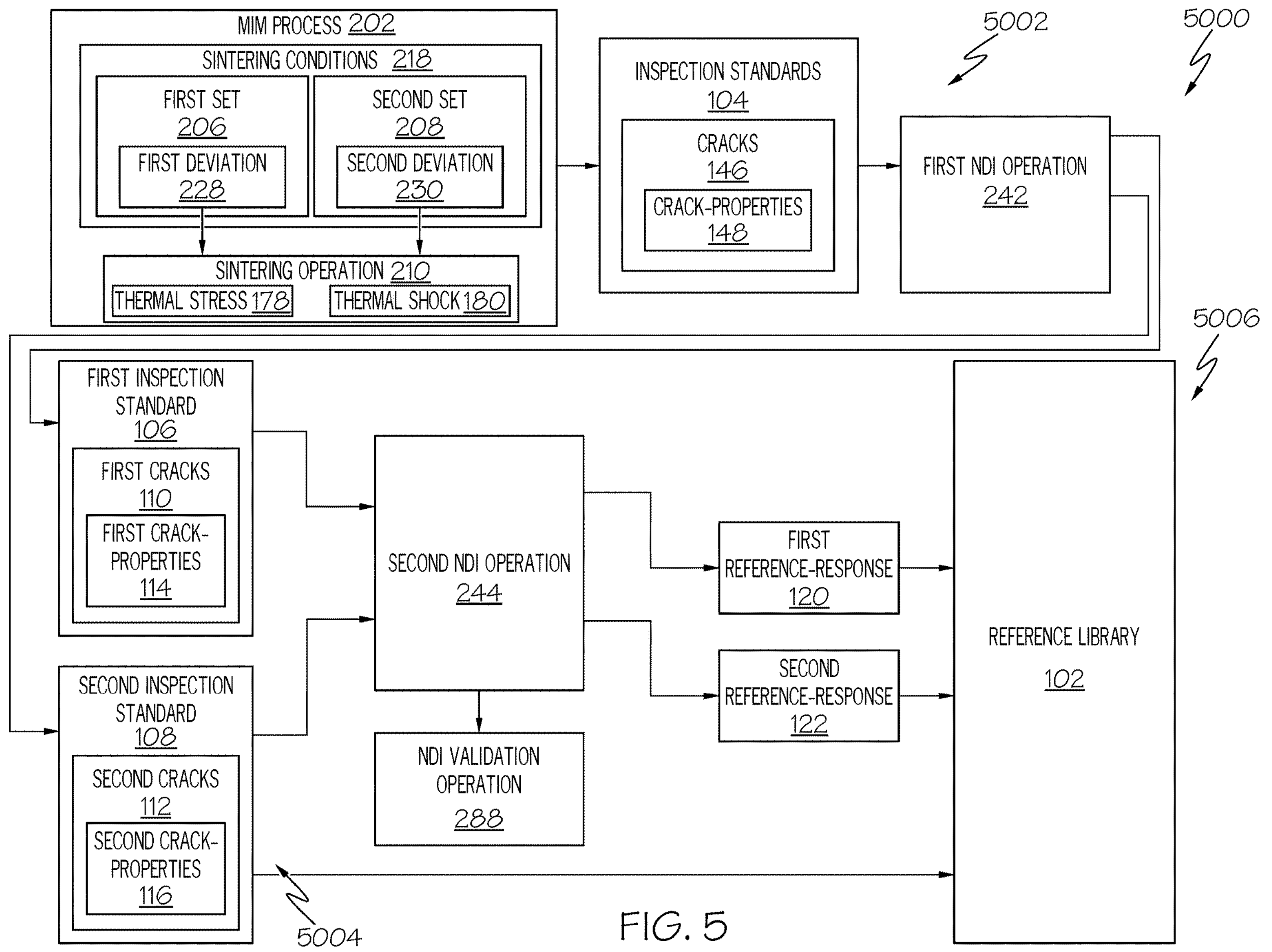
FIG. 5 is a block diagram of an example of a pre-inspection process.

The method 1000 includes a step of (block 1004) forming a second inspection standard 108 (e.g., as shown in FIG. 3). The second inspection standard 108 is formed using the metal injection molding process 200 (e.g., as shown in FIGS. 4 and 5).

The method 1000 includes a step of (block 1006) creating a reference library 102 (e.g., as shown in FIG. 3). The reference library 102 includes at least the first inspection standard 106 and the second inspection standard 108. In other examples, the reference library 102 includes any number of inspection standards 104 (e.g., as shown in FIG. 3).

In one or more examples, the first inspection standard 106 includes a first crack 110. The first crack 110 is induced by introducing at least one of a thermal shock 180 and a thermal stress 178 during a sintering operation 210 of the metal injection molding process 200 (e.g., as shown in FIGS. 4A, 4B, and 4C). Generally, the first crack 110 includes at least one first crack-property 114.

Reference is made throughout the present disclosure to examples of the first inspection standard 106 having the first crack 110. However, in other examples, the first inspection standard 106 includes a plurality of first cracks 110. In these examples, each one of the first cracks 110 includes one or more of the first crack-properties 114.

In one or more examples, the second inspection standard 108 includes a second crack 112. The second crack 112 is induced by introducing at least one of the thermal shock 180 and the thermal stress 178 during the sintering operation 210 of the metal injection molding process 200 (e.g., as shown in FIGS. 4A, 4B, and 4C). Generally, the second crack 112 includes at least one second crack-property 116.

Reference is made throughout the present disclosure to examples of the second inspection standard 108 having the second crack 112. However, in other examples, the second inspection standard 108 includes a plurality of second cracks 112. In these examples, each one of the second cracks 112 includes one or more of the second crack-properties 116.

In one or more examples, at least one of the thermal shock 180 and the thermal stress 178 introduced during the sintering operation 210 for the first inspection standard 106 is different than at least one of the thermal shock 180 and the thermal stress 178 introduced during the sintering operation 210 for the second inspection standard 108. As a result, the first crack 110 and the second crack 112 are different. As an example, the first crack-property 114 (e.g., at least one of the first crack-properties 114) and the second crack-property 116 (e.g., at least one of the second crack-properties 116) are different. For example, the first crack-property 114 of the first crack 110 and the second crack-property 116 of the second crack 112 is the same in kind but different in degree or measured parameter.

In one or more examples, the first crack 110 and the second crack 112 include at least one crack that is relatively large enough to enable detection. The crack is a result of stress from thermal expansion in a location in which a differential in temperature is the greatest. In one or more examples, the first crack 110 and the second crack 112 also include other cracks in adjacent areas, depending, for example, on a stress field, such as stress exceeding the strength at elevated temperature is what causes the fracture, and on the geometry of the manufactured inspection standard.

In one or more examples, the thermal shock 180 and/or the thermal stress 178, which results in formation of the first crack 110, occurs in response to or results from a first set 206 of sintering conditions 218 of the sintering operation 210. The thermal shock 180 and/or the thermal stress 178, which results in formation of second crack 112, occurs in response to or results from a second set 208 of the sintering conditions 218 of the sintering operation 210. As an example, at least one of the sintering conditions 218 in the second set 208 of the sintering conditions 218 is different than at least one of the sintering conditions 218 of the first set 206 of the sintering conditions 218.

In one or more examples, according to the method 1000, the step of (block 1002) forming the first inspection standard 106 includes a step of introducing a first deviation 228 (e.g., as shown in FIG. 5). In one or more examples, the first deviation 228 is introduced in the sintering conditions 218 of the sintering operation 210 of the metal injection molding process 200 during formation of the first inspection standard 106.

In one or more examples, according to the method 1000, the step of (block 1004) forming the second inspection standard 108 includes a step of introducing a second deviation 230 (e.g., as shown in FIG. 5). In one or more examples, the second deviation 230 is introduced in the sintering conditions 218 of the sintering operation 210 of the metal injection molding process 200 during formation of the second inspection standard 108.

The present disclosure recognizes that the sintering operation 210 has process limitations and includes a standard set of the sintering conditions 218, also referred to herein as operation conditions 324 (e.g., as shown in FIGS. 4A, 4B, and 4C). The operational conditions 324 include or refer to a set of the sintering conditions 218 that is typical for normal sintering and that is designed to produce a viable part according to a predetermined (e.g., design) specification, for example, having desired properties without defects outside of acceptable tolerances. In one or more examples, one of the properties of the part, according to the specification, is internal cracking, which refers to the type, shape, number, size, dimensions, and the like of internal cracks in the part. In these examples, defects refer to or include cracks having properties or parameters outside of an allowable tolerance of a predetermined threshold (e.g., based on the part specification).

Accordingly, in one or more examples, the first deviation 228 represents a first modification or change to the sintering conditions 218 (e.g., the operational conditions 324) of the sintering operation 210, for example, forming the first set 206 of the sintering conditions 218 that introduces a first instance of the thermal shock 180 and/or a first instance of the thermal stress 178, which results in the first crack 110 in the first inspection standard 106. Similarly, the second deviation 230 represents a second modification or change to the sintering conditions 218 (e.g., the operational conditions 324) of the sintering operation 210, for example, forming the second set 208 of the sintering conditions 218 that introduces a second instance of the thermal shock 180 and/or a second instance of the thermal stress 178, which results in the second crack 112 in the second inspection standard 108. As such, the first deviation 228 and the second deviation 230 are different.

In one or more examples, the sintering conditions 218 of the sintering operation 210 (e.g., as shown in FIG. 4B) include a sintering temperature 220, a sintering vacuum 222, and a sintering duration 224. In one or more examples, the sintering temperature 220 and the sintering duration 224 form or define a sintering profile 226. The sintering profile 226 includes or represents a heating rate 316 (e.g., an increase in the sintering temperature 220 over the sintering duration 224) and a cooling rate 318 (e.g., a decrease in the sintering temperature 220 over the sintering duration 224). As an example, the sintering profile 226 refers to a sintering temperature and duration profile that includes a ramp up temperature rate to the maximum sintering temperature and a ramp down temperature rate to ambient temperature (also referred to herein as a sintering temperature rate).

When manufacturing viable powder metal parts using the metal injection molding process 200 (e.g., as shown in FIGS. 4A, 4B, and 4C), parameters or values for the sintering conditions 218 for normal sintering are selected based on a number of factors, such as the design specification for the manufactured part. As an example, the sintering duration 224 is based on or is related to the mass of the part being sintered (e.g., the larger the mass, the longer the sintering duration 224). Likewise, the sintering temperature 220 is based on a temperature or temperature range needed to homogenize the part over the sintering duration 224.

In an example of normal sintering, the part may be heated to a homogenization temperature of approximately 2,200° F. to approximately 2,420° F. over a duration of approximately 1 to 3 hours and then held at that temperature for a duration of approximately 1 to 4 hours past homogenization and then cooled (e.g., the sintering profile 226). The heating rates 316 and the cooling rates 318 of the sintering profile 226 are selected to avoid thermal expansion that can result in defects, such as internal voids and cracks having properties outside of acceptable limits. Since there is no above atmospheric pressure applied in a vacuum furnace, the sintering vacuum 222 is generally in the range of the capability of a diffusion pump.

In one or more examples, the first deviation 228 and the second deviation 230 are introduced in the sintering profile 226 to induce the thermal stress 178 and/or the thermal shock 180. In these examples, the first deviation 228 refers to a first modification or adjustment of at least one of the sintering temperature 220 and the sintering duration 224. The second deviation 230 refers to a second modification or adjustment of at least one of the sintering temperature 220 and the sintering duration 224.

In one or more examples, the first deviation 228 and/or the second deviation 230 refer to or represent a transition between different sintering temperatures 220 over the sintering duration 224.

In one or more examples, the first deviation 228 and/or the second deviation 230 refer to or represent a change in the heating rate 316 of the sintering operation 210, for example, relative to an operational heating rate 294. The operational heating rate 294 refers to a heating rate that is typical for normal sintering.

In one or more examples, the first deviation 228 and/or the second deviation 230 refer to or represent a change in the cooling rate 318 of the sintering operation 210, for example, relative to an operational cooling rate 300. The operational cooling rate 300 refers to a cooling rate that is typical for normal sintering.

In one or more examples, the first deviation 228 and/or the second deviation 230 refer to or represent at a series of transitions (e.g., cycles) between different sintering temperatures 220 over the sintering duration 224.

In one or more examples, according to the method 1000, the step of (block 1002) forming the first inspection standard 106 includes a step of (block 1008) increasing the sintering temperature 220 during the sintering operation 210 at a first heating rate 290 (e.g., as shown in FIG. 4B) to introduce the thermal stress 178 in the first inspection standard 106. In one or more examples, the first heating rate 290 is greater than the operational heating rate 294 of the sintering operation 210. In one or more examples, the first heating rate 290 is less than the operational heating rate 294 of the sintering operation 210.

In one or more examples, according to the method 1000, the step of (block 1004) forming the second inspection standard 108 includes a step of (block 1010) increasing the sintering temperature 220 during the sintering operation 210 at a second heating rate 292 to introduce the thermal stress 178 in the second inspection standard 108. The second heating rate 292 is different than the first heating rate 290. In one or more examples, the second heating rate 292 is greater than the first heating rate 290. In one or more examples, the second heating rate 292 is less than the first heating rate 290.

In one or more examples, according to the method 1000, the step of (block 1002) forming the first inspection standard 106 includes a step of (block 1012) decreasing the sintering temperature 220 during the sintering operation 210 at a first cooling rate 296 (e.g., as shown in FIG. 4B) to introduce the thermal stress 178 in the first inspection standard 106. In one or more examples, the first cooling rate 296 is greater than the operational cooling rate 300 of the sintering operation 210. In one or more examples, the first cooling rate 296 is less than the operational heating rate 294 of the sintering operation 210. The operational cooling rate 300 refers to a cooling rate that is typical for normal sintering.

In one or more examples, according to the method 1000, the step of (block 1004) forming the second inspection standard 108 includes a step of (block 1014) decreasing the sintering temperature 220 during the sintering operation 210 at a second cooling rate 298 to introduce the thermal stress 178 in the second inspection standard 108. The second cooling rate 298 is different than the first cooling rate 296. In one or more examples, the second cooling rate 298 is greater than the first cooling rate 296. In one or more examples, the second cooling rate 298 is less than the first cooling rate 296.

Generally, the rate of change of the sintering temperature 220 (e.g., the operational heating rate 294 and/or the operational cooling rate 300) a normal sintering process is one where the rate of temperature increase and/or decrease is such that stress from thermal expansion in the part structure is lower than the strength of the part and the part will not crack after the sintering operation. A heating rate and/or cooling rate (e.g., heating rate 316 and cooling rate 318) that generate a desired defect (e.g., cracks) creates thermal expansion and resultant induces stress greater than the part structure strength at that temperature creating the crack (e.g., a kissing bond type crack). In one or more examples, the heating rate 316 and cooling rate 318 are modeled using a thermal finite element analysis (FEA) or boundary element analysis (BEA). In one or more examples, the heating rate 316 and cooling rate 318 are developed experimentally by conducting sintering trials for various part geometries and various temperature heating/cooling and degree of sintering (e.g., % of powder volume diffusion bonded within the cycle).

In one or more examples, according to the method 1000, the step of (block 1002) forming the first inspection standard 106 includes a step of (block 1016) cycling between a first sintering temperature 304 and a second sintering temperature 306 during the sintering operation 210 introduce the thermal stress 178. The first sintering temperature 304 and the second sintering temperature 306 are different. As an example, the second sintering temperature 306 is greater than the first sintering temperature 304.

In one or more example, the first inspection standard 106 is cycled between the first sintering temperature 304 and the second sintering temperature 306 a first number of cycles 302. As an example, the first number of cycles 302 is at least two cycles.

In one or more examples, according to the method 1000, the step of (block 1004) forming the second inspection standard 108 includes a step of (block 1018) cycling between a third sintering temperature 326 and a fourth sintering temperature 328 during the sintering operation 210 to introduce the thermal stress 178. The third sintering temperature 326 and the fourth sintering temperature 328 are different. As an example, the fourth sintering temperature 328 is greater than the third sintering temperature 326.

In one or more examples, the second inspection standard 108 is cycled between the third sintering temperature 326 and the fourth sintering temperature 328 a second number of the cycles 302. As an example, the second number of cycles 302 is at least two cycles.

In one or more examples, at least one of the first sintering temperature 304 and the second sintering temperature 306 is different than at least one of the third sintering temperature 326 and the fourth sintering temperature 328. In one or more examples, each of the first sintering temperature 304 and the second sintering temperature 306 is different than each of the third sintering temperature 326 and the fourth sintering temperature 328. As an example, the first sintering temperature 304 is greater than or less than the third sintering temperature 326 and the second sintering temperature 306 is greater than or less than the fourth sintering temperature 328.

In one or more examples, the second number of cycles 302 is different than the first number of the cycles 302. As an example, the second number of cycles 302 is greater than or less than the first number of the cycles 302. For example, a different number of the cycles 302 can be used when the first sintering temperature 304 and the second sintering temperature 306 are the same as or different than the third sintering temperature 326 and the fourth sintering temperature 328. In one or more examples, the second number of cycles 302 is the same as the first number of the cycles 302. For example, the same number of the cycles 302 can be used when the first sintering temperature 304 and the second sintering temperature 306 are different than the third sintering temperature 326 and the fourth sintering temperature 328.

In one or more examples, according to the method 1000, the step of (block 1002) forming the first inspection standard 106 includes a step of transitioning from a first minimum sintering temperature to a first maximum sintering temperature during the sintering operation 210 to introduce the thermal shock 180. In one or more examples, the transitioning step is performed multiple times. As an example, the step of (block 1002) forming the first inspection standard 106 includes a step of (block 1020) cycling between the first minimum sintering temperature and the first maximum sintering temperature during the sintering operation 210 to introduce the thermal shock 180.

In one or more examples, the first inspection standard 106 is cycled between first minimum sintering temperature and the first maximum sintering temperature the first number of the cycles 302.

In one or more examples, according to the method 1000, the step of (block 1004) forming the second inspection standard 108 includes a step of transitioning from a second minimum sintering temperature to a second maximum sintering temperature during the sintering operation 210 to introduce the thermal shock 180. In one or more examples, the transitioning step is performed multiple times. As an example, the step of (block 1004) forming the second inspection standard 108 includes a step of (block 1022) cycling between the second minimum sintering temperature and the second maximum sintering temperature during the sintering operation 210 to introduce the thermal shock 180.

In one or more examples, the second inspection standard 108 is cycled between the second minimum sintering temperature and the second maximum sintering temperature the second number of the cycles 302.

Values for the different sintering temperatures 220 described above (e.g., first sintering temperature 304, second sintering temperature 306, third sintering temperature 326, fourth sintering temperature 328, a minimum sintering temperature 320, and a maximum sintering temperature 322) may vary depending on the sintering temperatures 220 of the operational conditions 324 of the normal sintering operation. Generally, the different sintering temperatures 220 result in thermal expansion and, thus, a resultant thermal induced stress, that is greater than part strength at a given point in the sintering process (e.g., cycle 302).

In one or more examples, the first crack-property 114 is below a threshold crack-property 118 (e.g., as shown in FIG. 3). The second crack-property 116 is above the threshold crack-property 118. For example, a value or measurable parameter of the first crack-property 114 is less than a value or measurable parameter of the threshold crack-property 118 and a value or measurable parameter of the second crack-property 116 is greater than the value or measurable parameter of the threshold crack-property 118.

In one or more examples, at least one of the first crack-properties 114 is at least 10% less than the threshold crack-property 118 and at least one of the second crack-properties 116 is at least 10% greater than the threshold crack-property 118. In other examples, the first crack-property 114 in between approximately 5% and 15% less than the threshold crack-property 118 and the second crack-property 116 is between approximately 5% and 15% greater than the threshold crack-property 118. In yet other examples, the first crack-property 114 in between approximately 5% and 25% less than the threshold crack-property 118 and the second crack-property 116 is between approximately 5% and 25% greater than the threshold crack-property 118.

In one or more examples, the first crack-property 114 represents a lower limit or lower tolerance relative to the threshold crack-property 118 (e.g., 10% less than the threshold crack-property 118). The second crack-property 116 represents an upper limit or upper tolerance relative to the threshold crack-property 118 (e.g., 10% greater than the threshold crack-property 118). It can be appreciated that the values for the lower and upper limits from the threshold crack-property 118 represented by the first crack-property 114 and the second crack-property 116, respectively, depend on the measurable parameter of the void-properties (e.g., dimension, number, distribution, etc.).

Referring still to FIG. 1, in one or more examples, the method 1000 includes a step of (block 1024) performing a first nondestructive inspection (NDI) operation 242 on the first inspection standard 106. The first nondestructive inspection operation 242 of the first inspection standard 106 is configured to verify that the first crack-property 114 (e.g., at least one of the first crack-properties 114) is below the threshold crack-property 118.

The method 1000 includes a step of (block 1026) performing the first nondestructive inspection operation 242 on the second inspection standard 108. The first nondestructive inspection operation 242 on the second inspection standard 108 is configured to verify that the second crack-property 116 (e.g., at least one of the second crack-properties 116) is above the threshold crack-property 118.

In one or more examples, the first nondestructive inspection operation 242 is a visual nondestructive inspection methodology. In one or more examples, the first nondestructive inspection operation 242 is flash thermography. In other examples, the first nondestructive inspection operation 242 is one of computed tomography (CT), computed radiography (CR), digital radiography (DR), radiography testing (RT), and other suitable NDI mythologies.

Referring still to FIG. 1, in one or more examples, the method 1000 includes a step of (block 1028) performing a second nondestructive inspection (NDI) operation 244 on the first inspection standard 106. The second nondestructive inspection operation 244 on the first inspection standard 106 is configured to generate a first reference-response 120 (e.g., as shown in FIG. 5). The first reference-response 120 is representative of the first crack-property 114, as determined, verified, and/or validated by the first nondestructive inspection operation 242.

In one or more examples, the method 1000 includes a step of (block 1030) recording the first reference-response 120 to the second nondestructive inspection operation 244 associated with the first inspection standard 106.

In one or more examples, the method 1000 includes a step of (block 1032) performing the second nondestructive inspection operation 244 on the second inspection standard 108. The second nondestructive inspection operation 244 on the second inspection standard 108 is configured to generate a second reference-response 122 (e.g., as shown in FIG. 5). The second reference-response 122 is representative of the second crack-property 116, as determined, verified, and/or validated by the first nondestructive inspection operation 242.

In one or more examples, the method 1000 includes a step of (block 1034) recording the second reference-response 122 to the second nondestructive inspection operation 244 associated with the second inspection standard 108.

In one or more examples, the second nondestructive inspection operation 244 is a non-visual nondestructive inspection methodology. In one or more examples, the second nondestructive inspection operation 244 is a resonant acoustic method. In other examples, the second nondestructive inspection operation 244 is ultrasonic testing (UT) or other suitable method NDI methodologies.

In one or more examples, the step of (block 1006) creating the reference library 102 includes a step of cataloging and physically storing the first inspection standard 106 and the second inspection standard 108. In one or more examples, the step of (block 1006) creating the reference library 102 includes a step of storing the first reference-response 120 and the second reference-response 122 on a digital storage device, such as a database 156 (e.g., shown in FIG. 3).

In one or more examples, upon creation of the reference library 102, the reference library 102 can be used to qualify or validated powder metal parts (e.g., parts made using the powder metallurgy process 246) using the second nondestructive inspection operation 244.

Referring still to FIG. 1, in one or more examples, the method 1000 includes a step of (block 1036) forming a part 124. The part 124 is formed (e.g., manufactured, fabricated, or otherwise produced) using the powder metallurgy process 246 (e.g., as shown in FIG. 6). The part 124 includes any metallic structure made using metal powder. In one or more examples, the part 124 is a standalone metallic structure. In one or more examples, the part 124 is a metallic component of another structure.

Generally, the inspection standards 104, such as the first inspection standard 106 and the second inspection standard 108 (e.g., as shown in FIG. 3), have substantially the same geometry (e.g., near-net shape or net shape) as the part 124 and substantially the same material composition as the part 124. Fabricating inspection standards 104 having substantially the same geometry and material composition as the parts 124 to be inspected provide substantially similar signal-to-noise ratios during inspection, which, as described herein, can be analyzed using algorithms for specific part shapes and reduce false inspection results.

In some implementations, the part 124 may be made using a powder metallurgy process other than metal injection molding. In one or more examples, as illustrated in FIG. 6, the powder metallurgy process 246 used to form the part 124 includes one of the metal injection molding process 200, an additive manufacturing process 248 (e.g., powder bed fusion, cold spraying, thermal spraying, etc.), and an isostatic pressing process 250 (e.g., cold isostatic pressing or hot isostatic pressing). Other examples of the powder metallurgy process 246 include, but are not limited to, die pressing and sintering.

Figure 10:
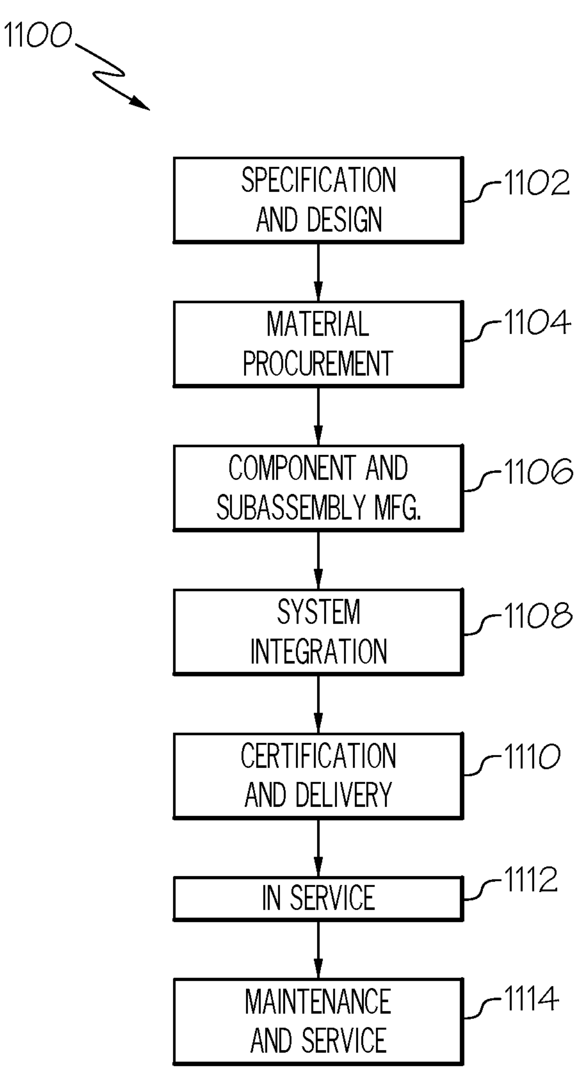
FIG. 10 is a flow diagram of an example of an aircraft service method.

In one or more examples, the step of (block 1036) forming the part 124 is a step of a larger manufacturing process, such as an aircraft manufacturing and service method 1100 (e.g., shown in FIG. 10). It can be appreciated that implementations of the manufacturing process can be used to manufacture any number of parts 124.

In one or more examples, the method 1000 includes a step of (block 1038) performing the second nondestructive inspection operation 244 on the part 124. The second nondestructive inspection operation 244 on the part 124 is configured to generate an inspection-response 126 (e.g., as shown in FIG. 6). The inspection-response 126 is representative of a crack-property 148 (e.g., at least one of a plurality of crack-properties 148) of a crack 146 (e.g., at least one of a plurality of cracks 146) in the part 124.

In one or more examples, the method 1000 includes a step of (block 1040) recording the inspection-response 126 to the second nondestructive inspection operation 244 associated with the part 124.

In one or more examples, the method 1000 includes a step of (block 1042) comparing the inspection-response 126 to the first reference-response 120 and the second reference-response 122. Results from the comparing step (block 1042) are used to qualify the part 124 as passing (block 1044) the nondestructive inspection (e.g., being viable part) or as failing (block 1046) the nondestructive inspection (e.g., being a defective part).

As an example, the first reference-response 120 represents the value or measurable parameter of the first crack-property 114, which is a lower limit of an acceptable tolerance for the part 124 (e.g., a lower limit of the threshold crack-property 118).

As an example, the second reference-response 122 represents the value or measurable parameter of the second crack-property 116, which is an upper limit of the acceptable tolerance for the part 124 (e.g., an upper limit of the threshold crack-property 118).

As an example, the inspection-response 126 represents the value or measurable parameter of the crack-property 148 of the part 124, as manufactured.

In one or more examples, during the step of (block 1042) comparing, if the inspection-response 126 is between (e.g., bound, inclusively or exclusively, by) the first reference-response 120 and the second reference-response 122, then the part 124 passes inspection (block 1044). However, if the inspection-response 126 is outside of (e.g., exceeds) one of the first reference-response 120 and the second reference-response 122, then the part 124 fails inspection (block 1046).

Referring now to FIG. 2, which illustrates an example of a method 2000. The method 2000 is an example of the disclosed methods for non-destructive inspecting of the parts 124 (e.g., as shown in FIG. 3).

Implementations of the method 2000 provide for creation of the nondestructive inspection standards 104 that can be used as references to qualify of validate results of nondestructive inspection of the part 124. Creation of the inspection standards 104 also enable selection and validation of different nondestructive inspection methodologies, which can be used to nondestructively inspect the part 124.

In one or more examples, the method 2000 includes a step of (block 2002) forming a plurality of the inspection standards 104. Each one of the inspection standards 104 is formed (e.g., manufactured, fabricated, or otherwise produced) using the metal injection molding process 200 (e.g., as shown in FIGS. 4A, 4B, and 4C).

In one or more examples, the method 2000 includes a step of (block 2004) manipulating at least one of the sintering conditions 218 (e.g., as shown in FIG. 4B) of the sintering operation 210 of the metal injection molding process 200.

Manipulation of at least one of the sintering conditions 218 (e.g., block 2004) is configured to induce the crack 146 (e.g., at least one crack 146) in each one of the inspection standards 104 during formation (e.g., block 2002). Accordingly, in one or more examples, the step of (block 2004) manipulating the sintering conditions 218 is performed during (e.g., concurrent with) the step of (block 2002) forming the inspection standards 104 using the metal injection molding process 200.

In one or more examples, the method 2000 includes a step of (block 2006) introducing the thermal shock 180 during the sintering operation 210 of the metal injection molding process 200. The thermal shock 180 results from the step of (block 2004) manipulating the sintering conditions 218. The thermal shock 180 induces the crack 146 in each one of the inspection standards 104.

In one or more examples, in one or more examples, the method 2000 includes a step of (block 2008) introducing the thermal stress 178 during the sintering operation 210 of the metal injection molding process 200. The thermal stress 178 results from the step of (block 2004) manipulating the sintering conditions 218. The thermal shock 180 induces the crack 146 in each one of the inspection standards 104.

In one or more examples, in one or more examples, the method 2000 includes a combination of the step of (block 2006) introducing the thermal shock 180 and the step of (block 2008) introducing the thermal stress 178 during the sintering operation 210 of the metal injection molding process 200 to induce the crack 146 in each one of the inspection standards 104

In one or more examples, according to the method 2000, the step of (block 2004) manipulating at least one of the sintering conditions 218 of the sintering operation 210 includes a step of introducing a deviation 252 (e.g., as shown in FIG. 4B) in the sintering conditions 218. As an example, the deviation 252 is introduced in at least one of the sintering temperature 220 and the sintering duration 224 (e.g., the sintering profile 226). The step of introducing the deviation 252 occurs or is performed during the step of (block 2002) forming each one of the inspection standards 104.

As described above, with respect to examples of the method 1000, one or more of the deviations 252 (e.g., as shown in FIG. 4B) are applied to one or more of the sintering conditions 218 to introduce or otherwise induce at least one of the thermal shock 180 and the thermal stress 178 in the inspection standard 104 during the sintering operation 210 of the metal injection molding process 200.

In one or more examples, a batch of the inspection standards 104 is produced, in which each one of the inspection standards 104 of the batch is formed using different deviations 252 and, thus, different sintering conditions 218. As such, each one of the inspection standards 104 may include the cracks 146 having different crack-properties 148 (e.g., as shown in FIG. 5).

Referring still to FIG. 2, in one or more examples, according to the method 2000, the step of (block 2008) introducing the thermal stress 178 includes a step of increasing the sintering temperature 220 during the sintering operation 210 at the heating rate 316 that is greater than the operational heating rate 294 of the sintering operation 210.

In one or more examples, according to the method 2000, the step of (block 2008) introducing the thermal stress 178 includes a step of decreasing the sintering temperature 220 during the sintering operation 210 at the cooling rate 318 that is greater than the operational cooling rate 300 of the sintering operation 210.

In one or more examples, according to the method 2000, the step of (block 2008) introducing the thermal stress 178 includes a step of increasing the sintering temperature 220 during the sintering operation 210 at the heating rate 316 that is greater than the operational heating rate 294 of the sintering operation 210.

In one or more examples, according to the method 2000, the step of (block 2008) introducing the thermal stress 178 includes a combination of the step of increasing the sintering temperature 220 during the sintering operation 210 at the heating rate 316 that is greater than the operational heating rate 294 of the sintering operation 210 and the step of decreasing the sintering temperature 220 during the sintering operation 210 at the cooling rate 318 that is greater than the operational cooling rate 300 of the sintering operation 210.

In one or more examples, according to the method 2000, the step of (block 2008) introducing the thermal stress 178 includes a step of cycling between different sintering temperatures 220 during the sintering operation 210 a number of the cycles 302. In one or more examples, the step of (block 2008) introducing the thermal stress 178 includes a step of cycling between different temperatures (e.g., different sintering temperatures 220) during interruption of the sintering operation 210 a number of the cycles 302. As an example, the sintering temperature 220 is cycled between the first sintering temperature 304 and the second sintering temperature 306. As another example, the sintering temperature 220 is cycled between the third sintering temperature 326 and the fourth sintering temperature 328.

In one or more examples, according to the method 2000, the step of (block 2006) introducing the thermal shock 180 includes a step of cycling between a minimum sintering temperature 320 and a maximum sintering temperature 322 during the sintering operation 210. In one or more examples, the step of (block 2006) introducing the thermal shock 180 includes a step of cycling between a minimum temperature (e.g., the minimum sintering temperature 320) and a maximum temperature (e.g., the maximum sintering temperature 322) at a rate higher than a sintering temperature rate (e.g., a sintering temperature rate typical for normal sintering) during interruption of the sintering operation 210. As an example, the sintering temperature 220 is transitioned or cycled between the first minimum sintering temperature and the first maximum sintering temperature. As another example, the sintering temperature 220 is transitioned or cycled between the second minimum sintering temperature and the second maximum sintering temperature.

In one or more examples, the first sintering temperature 304 and the third sintering temperature 326 are examples of the minimum sintering temperature 320 (e.g., as shown in FIG. 4B). In one or more examples, the second sintering temperature 306 and the fourth sintering temperature 328 are examples of the maximum sintering temperature 322 (e.g., as shown in FIG. 4B).

Referring still to FIG. 2, in one or more examples, the method 2000 includes a step of (block 2010) performing the first nondestructive inspection operation 242 (e.g., as shown in FIG. 5) on each one of the inspection standards 104. The step of (block 2010) performing the first nondestructive inspection operation 242 is configured to determine at least one of the crack-properties 148 of the cracks 146 of each one of the inspection standards 104.

As an example, the first nondestructive inspection operation 242 (e.g., a visual NDI methodology) quantifies (e.g., provides values or measurable parameters of) one or more of the crack-properties 148 of the cracks 146 for each one of the inspection standards 104.

In one or more examples, the method 2000 includes a step of (block 2012) selecting a first one of the inspection standards 104 (e.g., the first inspection standard 106 shown in FIG. 5). In these examples, the first inspection standard 106 refers to a first one of the inspection standards 104 in which at least one of the crack-properties 148 of the cracks 146 (e.g., the first crack-property 114 of the first crack 110) is below the threshold crack-property 118, for example, as determined by the first nondestructive inspection operation 242.

In one or more examples, the method 2000 includes a step of (block 2014) selecting a second one of the inspection standards 104 (e.g., the second inspection standard 108 shown in FIG. 5). In these examples, the second inspection standard 108 refers to one of the inspection standards 104 in which at least one of the crack-properties 148 of the cracks 146 (e.g., the second crack-property 116 of the second crack 112) is above the threshold crack-property 118, for example, as determined by the first nondestructive inspection operation 242.

As an example, the threshold crack-property 118 is a value or measurable parameter of the cracks represented in a viable part, for example, according to a predetermined specification for the part. Manufactured parts that have cracks with crack-properties substantially the same as the threshold crack-property 118 or within an acceptable tolerance of the threshold crack-property 118 are considered viable. Manufactured parts that have cracks with crack-properties that vary from the threshold crack-property 118 or that are outside of the acceptable tolerance of the threshold crack-property 118 are considered defective.

Accordingly, results from the first nondestructive inspection operation 242 enable selection of certain ones of the inspection standards 104 that have crack-properties that are relevant and proximate to (e.g., within an allowable tolerance of) the threshold crack-property 118. In the examples above, the first inspection standard 106 is selected because the first crack-property 114 of the first crack 110 in the first inspection standard 106 has a value or measurable parameter that represents a lower limit of an acceptable variation from (e.g., 10% less than) the threshold crack-property 118. Similarly, the second inspection standard 108 is selected because the second crack-property 116 of the second crack 112 in the second inspection standard 108 has a value or measurable parameter that represents an upper limit of an acceptable variation from (e.g., 10% greater than) the threshold crack-property 118.

It can be appreciated that any number of inspection standards 104 may be qualified as representing acceptable boundaries of the threshold crack-property 118. As an example, a first set of (e.g., at least two) inspection standards 104 can be selected to represent a first range (e.g., 10%) from the threshold crack-property 118 and a second set of inspection standards 104 can be selected to represent a second range (e.g., 15%) from the threshold crack-property 118. As another example, a first set of inspection standards 104 can be selected to represent a first one of a plurality of threshold crack-properties 118 (e.g., dimension) and a second set of inspection standards 104 can be selected to represent a second one of the plurality of threshold crack-properties 118 (e.g., number).

Referring still to FIG. 2, in one or more examples, the method 2000 includes a step of (block 2016) performing the second nondestructive inspection operation 244 on the first inspection standard 106 (e.g., the selected first one of the inspection standards 104). The second nondestructive inspection operation 244 on the first inspection standard 106 is configured to generate the first reference-response 120 that is representative of at least one of the crack-properties 148 (e.g., first crack-property 114), as determined, validated, or verified by the first nondestructive inspection operation 242.

In one or more examples, the method 2000 includes a step of (block 2018) recording the first reference-response 120 to the second nondestructive inspection operation 244 associated with the first inspection standard 106. In one or more examples, the method 2000 can also include a step of storing the first reference-response 120 in the reference library 102 (e.g., the database 156 shown in FIG. 3).

In one or more examples, the method 2000 includes a step of (block 2020) performing the second nondestructive inspection operation 244 on the second inspection standard 108 (e.g., the selected second one of the inspection standards 104). The second nondestructive inspection operation 244 on the second inspection standard 108 is configured to generate the second reference-response 122 that is representative of at least one of the crack-properties 148 (e.g., second crack-properties 116), as determined, validated, or verified by the first nondestructive inspection operation 242.

In one or more examples, the method 2000 includes a step of (block 2022) recording the second reference-response 122 to the second nondestructive inspection operation 244 associated with the second inspection standard 108. In one or more examples, the method 2000 can also include a step of storing the second reference-response 122 in the reference library 102 (e.g., the database 156 shown in FIG. 3).

In one or more examples, the second nondestructive inspection operation 244 is any suitable non-visual nondestructive inspection methodology. As an example, the second nondestructive inspection operation 244 is the resonant acoustic method. In this example, the first inspection standard 106 is excited by a known and repeatable force input (e.g., a ping or spectrum sweep). The first reference-response 120 is acquired using a dynamic sensor (e.g., microphone or accelerometer). A time-based data frequency domain for the first reference-response 120 is converted (e.g., by Fast Fourier Transform (FFT)). A frequency spectrum for the first reference-response 120 is analyzed and correlated with the results from the first nondestructive inspection operation 242, such that the first reference-response 120 represents the first crack-property 114 of the first crack 110. This process is repeated for the second inspection standard 108, such that the second reference-response 122 represents the second crack-property 116 of the second crack 112.

In one or more examples, the method 2000 includes a step of (block 2024) generating the reference library 102. In one or more examples, the reference library 102 takes the form of a catalog of physical inspection standards or coupons and includes at least the first one of the inspection standards 104 (e.g., the first inspection standard 106) and the second one of the inspection standards 104 (e.g., the second inspection standard 108). In one or more examples, the reference library 102 takes the form of a database storing the responses associated with the inspection standards 104 and includes the first reference-response 120 associated with the first inspection standard 106 and the second reference-response 122 associated with the second inspection standard 108.

Accordingly, in one or more examples, the step of (block 2024) generating the reference library 102 includes a step of cataloging and physically storing the first inspection standard 106 and the second inspection standard 108. In one or more examples, the step of (block 2028) generating the reference library 102 includes a step of storing the first reference-response 120 and the second reference-response 122 on a digital storage device, such as a computing device 154 or a database 156 (e.g., shown in FIG. 3).

In one or more examples, upon creation of the reference library 102, the reference library 102 can be used to qualify or validate the parts 124 (e.g., powder metal parts made using the powder metallurgy process 246) using the second nondestructive inspection operation 244.

Referring still to FIG. 2, in one or more examples, the method 2000 includes a step of (block 2026) forming the part 124. The part 124 is formed using the powder metallurgy process 246 (e.g., as shown in FIG. 6).

In one or more examples, the method 2000 includes a step of (block 2028) performing the second nondestructive inspection operation 244 on the part 124. The second nondestructive inspection operation 244 on the part 124 is configured to generate the inspection-response 126 that is representative of at least one of the crack-properties 148 of at least one of the cracks 146 in the part 124.

In one or more examples, the method 2000 includes a step of (block 2030) recording the inspection-response 126 to the second nondestructive inspection operation 244 associated with the part 124. In one or more examples, the method 2000 can also include a step of storing the inspection-response 126 (e.g., by the computing device 154 as shown in FIG. 3).

The method 2000 includes a step of (block 2032) comparing the inspection-response 126 to the first reference-response 120 and the second reference-response 122. Results from the comparing step (block 2032) are used to qualify the part 124 as passing (block 2034) the nondestructive inspection (e.g., being viable part) or as failing (block 2036) the nondestructive inspection (e.g., being a defective part).

As an example, the part 124 is inspected using the second nondestructive inspection operation 244, such as resonant acoustic method. In this example, the part 124 is excited by the known and repeatable force input (e.g., a ping or spectrum sweep). The inspection-response 126 is acquired using the dynamic sensor (e.g., microphone or accelerometer). A time-based data frequency domain for the inspection-response 126 is converted (e.g., by Fast Fourier Transform (FFT)). A frequency spectrum for the inspection-response 126 is analyzed for the part 124. The frequency spectrum (e.g., spectral signature) of the inspection-response 126 (e.g., representing the part 124) is compared to the frequency spectrum of the first reference-response 120 and the frequency spectrum of the second reference-response 122. If the frequency spectrum of the inspection-response 126 is substantially the same as or is within the frequency spectrums of the first reference-response 120 and the second reference-response 122, then the part 124 passes inspection and is deemed a viable part. If the frequency spectrum of the inspection-response 126 is different than or is outside of the frequency spectrums of the first reference-response 120 and the second reference-response 122, then the part 124 fails inspection and is deemed a defective part.

As such, creating and using the inspection standards 104 and selecting and using an appropriate type of the second nondestructive inspection operation 244 (e.g., as described in the method 1000 and the method 2000) enables rapid and economically efficient nondestructive testing of parts 124 made using the powder metallurgy process 246 on a mass scale.

Referring now to FIG. 3, which schematically illustrates an example of a system 100. The system 100 is an example of the disclosed systems for non-destructive testing the parts 124. The system 100 provides the inspection standards 104 that can be used as references to qualify or validate results of nondestructive inspection of the parts 124. The inspection standards 104 also enable selecting and validating different nondestructive inspection methodologies, which can be used to nondestructively inspect the part 124.

In one or more examples, the system 100 includes the reference library 102. In one of more examples, the reference library 102 takes the form of a physical inspection standard catalog. As an example, the reference library 102 includes at least the first inspection standard 106 and the second inspection standard 108. The first inspection standard 106 and the second inspection standard 108 are formed by the metal injection molding process 200.

In other examples, the reference library 102 includes any number of the inspection standards 104. Sets (e.g., two or more) of the inspection standards 104 can be associated or used as qualification reference standards with each one of any number of different types of parts 124, such as parts 124 made using different powder feedstock 144, parts 124 made using different powder metallurgy processes 246, parts 124 having different geometries, parts 124 having different threshold crack-properties 118, and the like.

In one or more examples, the reference library 102 takes the form of the database 156. As an example, the reference library 102 (e.g., the database 156) includes (e.g., stores) a plurality of reference-responses 158 associated with each one of the inspection standards 104 as generated by the second nondestructive inspection operation 244. In one or more examples, the reference library 102 (e.g., the database 156) includes (e.g., stores) the first reference-response 120, associated with the first inspection standard 106, and the second reference-response 122, associated with the second inspection standard 108.

Each one of the inspection standards 104 includes the crack 146 (e.g., at least one crack). The crack 146 include the crack-property 148 (e.g., at least one crack-property). The crack 146, having the crack-property 148, is induced or otherwise intentionally formed in the each one of the inspection standards 104 by manipulating the sintering conditions 218 of the sintering operation 210 of the metal injection molding process 200 (e.g., shown in FIGS. 4A, 4B, and 4C), for example, as described above with reference to the method 1000 and/or the method 2000.

In one or more examples, the first inspection standard 106 includes the first crack 110. The first crack 110 is induced or otherwise intentionally formed in the first inspection standard 106 by the first set 206 of the sintering conditions 218 of the sintering operation 210 of the metal injection molding process 200 (e.g., as shown in FIG. 5). As an example, the first crack 110 is induced by introducing at least one of the thermal shock 180 and the thermal stress 178 during the sintering operation 210 of the metal injection molding process 200.

In one or more examples, the second inspection standard 108 includes the second crack 112. The second crack 112 are induced or otherwise intentionally formed in the second inspection standard 108 by the second set 208 of the sintering conditions 218 of the sintering operation 210 (e.g., as shown in FIG. 5). As an example, the second crack 112 is induced by introducing at least one of the thermal shock 180 and the thermal stress 178 during the sintering operation 210 of the metal injection molding process 200.

In one or more examples, at least one of the sintering conditions 218 in the second set 208 of the sintering conditions 218 is different than at least one of the sintering conditions 218 of the first set 206 of the sintering conditions 218. In one or more examples, the first crack 110 include at least the first crack-property 114 that is below the threshold crack-property 118. In one or more examples, the second crack 112 include at least the second crack-property 116 that is above the threshold crack-property 118.

In one or more examples, the system 100 includes a first nondestructive inspection (NDI) device 150. The first NDI device 150 is configured to perform the first NDI operation 242 (e.g., as shown in FIG. 5). As an example, the first NDI device 150 is configured to nondestructively inspect the first inspection standard 106. The first NDI device 150 is configured to nondestructively inspect the second inspection standard 108.

The first NDI device 150 is configured to quantify (e.g., visually) the first crack-property 114 and/or to qualitatively verify that the first crack-property 114 is below (e.g., defining an acceptable lower limit of) the threshold crack-property 118. The first NDI device 150 is configured to quantify (e.g., visually) the second crack-property 116 and/or to qualitatively verify that the second crack-property 116 is above (e.g., defining an acceptable upper limit) the threshold crack-property 118.

In one or more examples, the system 100 includes a second nondestructive inspection (NDI) device 152. The second NDI device 152 is configured to perform the second NDI operation 244 (e.g., as shown in FIGS. 5 and 6). As an example, the second NDI device 152 is configured to nondestructively inspect the first inspection standard 106. The second NDI device 152 is configured to nondestructively inspect the second inspection standard 108. The second NDI device 152 is configured to produce the first reference-response 120 associated with the first crack-property 114 of the first inspection standard 106. The second NDI device 152 is configured to produce the second reference-response 122 associated with the second crack-property 116 of the second inspection standard 108.

In one or more examples, the system 100 includes the computing device 154. In one or more examples, the computing device 154 is configured to store the first reference-response 120 and the second reference-response 122. As an example, the first reference-response 120 and the second reference-response 122 are provided (e.g., transmitted or otherwise communicated) from the second nondestructive inspection device 152 to the computing device 154. In one or more examples, the first reference-response 120 and the second reference-response 122 are stored in memory of the computing device 154. In one or more examples, the first reference-response 120 and the second reference-response 122 are stored in the database 156, which is in communication with the computing device 154.

In one or more examples, the second NDI device 152 is configured to and is used to nondestructively inspect the part 124 formed by the powder metallurgy process 246. The second NDI device 152 is configured to produce the inspection-response 126 associated the crack-property 148 of the crack 146 in the part 124.

In one or more examples, the computing device 154 is configured to analyze the inspection-response 126, the first reference-response 120, and the second reference-response 122. As an example, the computing device 154 is configured to compare the inspection-response 126 to the first reference-response 120 and to the second reference-response 122. For example, the computing device 154 is configured to perform an inspection operation 272 (e.g., as shown in FIG. 6) in which the inspection-response 126 is compared to the first reference-response 120 and to the second reference-response 122. Based on the results of the inspection operation 272, the part 124 either passes or fails inspection.

Referring now to FIGS. 4A, 4B, and 4C (also collectively referred to herein as FIG. 4), which schematically illustrates an example of a metal injection molding (MIM) system 202. The metal injection molding system 202 is configured to perform the metal injection molding process 200 to form a final consolidated part having a desired density and porosity. In one or more examples, the inspection standards 104 (e.g., shown in FIG. 3) are formed using the metal injection molding process 200 (e.g., like that shown in FIG. 4).

In one or more examples, metal powder 160 and a binder 162 are provided to a mixing apparatus 254. The mixing apparatus 254 is configured to perform a mixing operation 280 in which the metal powder 160 and the binder 162 are combined into a homogeneous mixture to produce the powder feedstock 144.

The metal powder 160 includes fine powder of any suitable metal or metal alloy, including, but not limited to, iron, steel, copper, stainless steel, titanium, aluminum, nickel, tin, molybdenum, tungsten, tungsten carbide, various precious metals, or combinations and alloys thereof. In one or more examples, the binder 162 is a polymeric binder (e.g., thermoplastic).

The powder feedstock 144 is provided to an injection molding apparatus 256. The injection molding apparatus 256 is configured to perform an injection molding operation 282 in which one or more injection molding machines inject the powder feedstock 144 into one or more molds to form a green part 258.

The green part 258 is provided to a debinding apparatus 260. The debinding apparatus 260 is configured to perform a debinding operation 284 in which the binder 162 is removed from the molded green part 258, leaving behind a brown part 262 that retains the molded shape. In one or more examples, the binder 162 is removed by solvent debinding. In one or more examples, the binder 162 is removed by thermal debinding. Solvent debinding and thermal debinding may be performed by discrete operations and machines. Thermal debinding may also include presintering.

The brown part 262 is provided to a sintering apparatus 212. The sintering apparatus 212 is configured to perform the sintering operation 210 in which the brown part 262 is sintered and the metal powder particles are bonded together to form a sintered part 264. In one or more examples, the thermal debinding operation and the sintering operation are both performed by the sintering apparatus 212.

Generally, powder metal parts are manufactured using the sintering conditions 218 of the sintering operation 210, as described above. In one or more examples, the parts 124 are manufactured using the operational conditions 324 for the sintering operation 210, as described above. In one or more examples, the inspection standards 104 (e.g., the first inspection standard 106 and the second inspection standard 108) are manufactured using the sintering conditions 218 as modified by the deviations 252, as described above. As illustrated in FIG. 4, in one or more examples, one or more deviations 252 are introduced to the sintering conditions 218 of the sintering operation 210 to form each one of the plurality of inspection standards 104 (e.g., as shown in FIG. 3).

The sintered part 264 is provided to a hot isostatic pressing (HIP) apparatus 216. The HIP apparatus 216 is configured to perform a hot isostatic pressing (HIP) operation 214 in which the porosity of the part is reduced, and the density of the part is increased to form a hot isostatic pressed (HIP) part 266 (e.g., a final consolidated part having a desired density and porosity).

Generally, powder metal parts are manufactured using hot isostatic pressing (HIP) conditions 232 of the HIP operation 214. In one or more examples, the (HIP) conditions 232 of the HIP operation 214 include a hot isostatic pressing (HIP) temperature 234, a hot isostatic pressing (HIP) pressure 236, and a hot isostatic pressing (HIP) duration 238. In one or more examples, the HIP temperature 234 and the HIP duration 238 form or define a hot isostatic pressing (HIP) profile 240.

When manufacturing viable powder metal parts using the metal injection molding process 200 (e.g., like that shown in FIG. 4), parameters or values for the HIP conditions 232 for normal hot isostatic pressing are selected based on a number of factors, such as the design specification for the manufactured part. For example, values for the HIP temperature 234, the HIP pressure 236, and the HIP duration 238 for normal hot isostatic pressing may be based on the mass and/or dimensions of the part and the time, pressure, and duration required for sufficiently reduce porosity and increase density of the part. As an example, the HIP temperature 234 for normal hot isostatic pressing is between approximately 1,650° F. and approximately 1,750° F. As an example, the HIP pressure for normal hot isostatic pressing is at least approximately 14,500 psi. As an example, the HIP duration 238 for normal hot isostatic pressing is between approximately 2 and 4 hours.

Optionally, the HIP part 266 can be provided to a heat treating apparatus 268. The heat treating apparatus 268 is configured to perform a heat treating operation 286 on the HIP part 266 and produce a heat treated part 270.

The example of the metal injection molding system 202 and/or metal injection molding process 200 illustrated in FIG. 4 are exemplary of known metal injection molding methodologies. It can be appreciated that, in other examples, additional or alternative apparatuses and/or operations may be included as known in the art.

Referring now to FIG. 5, which schematically illustrates an example of a pre-inspection process 5000. The process 5000 represents portions of or certain operation steps described and illustrated with respect to the method 1000 (FIG. 1) and the method 2000 (FIG. 2). As an example, the process 5000 describes or may be referred to as a method for fabricating the inspection standards 104 and generating the reference library 102 for nondestructive inspection.

The process 5000 includes a production phase 5002 in which the inspection standards 104 are produced. The process 5000 includes a validation phase 5004 in which the inspection standards 104 are validated and relevant ones of the inspection standards 104 are selected (e.g., the first inspection standard 106 and the second inspection standard 108). The process 5000 also includes a reference phase 5006 in which the reference library 102 is created.

As illustrated, in one or more examples, a number of inspection standards 104 are produced using the metal injection molding process 200 (e.g., as also shown in FIG. 4). Each one of the inspection standards 104 includes at least one crack 146 having at least one of the crack-properties 148 formed by introduction of at least one of the thermal stress 178 and the thermal shock 180 resulting from the deviations 252 (e.g., first deviation 228 and the second deviation 230) or other variations in the sintering conditions 218 of the sintering operation 210.

The first NDI operation 242 is performed on each one of the inspection standards 104. The results of the first NDI operation 242 are analyzed and used to select relevant ones of the inspection standards 104, such as the first inspection standard 106 and the second inspection standard 108.

The second NDI operation 244 is performed on the first inspection standard 106. The results of the second NDI operation 244 form the first reference-response 120. The first reference-response 120 is analyzed and correlated to the results of the first NDI operation 242. The first reference-response 120 is stored in the reference library 102.

The second NDI operation 244 is performed on the second inspection standard 108. The results of the second NDI operation 244 form the second reference-response 122. The second reference-response 122 is analyzed and correlated to the results of the first NDI operation 242. The second reference-response 122 is stored in the reference library 102.

In one or more examples, the process 5000 also includes an NDI validation operation 288. In these examples, a plurality of different types of nondestructive inspection methodologies (e.g., resonant acoustic method, ultrasonic testing, and other suitable non-visual NDI methods) are performed on the first inspection standard 106 and the second inspection standard 108. The first reference-response 120 and the second reference-response 122 generated by each one of the different nondestructive inspection methodologies are validated based on comparisons to the results the first NDI operation 242. As an example, a first type of NDI methodology may be capable of providing a required level of sensitivity to represent a particular type of crack-property 148 or a desired range of tolerance with respect to the threshold crack-property 118 in the reference-response, while a second type of NDI methodology may not be capable of such sensitivity. In this example, validation suggests use of the first type of NDI methodology for the second NDI operation 244.

In one or more examples, the NDI-methodology evaluation process is specifically tuned to the geometry, mass, moment of inertia natural frequency, etc. of the part to which the NDI methodology is to be applied, so that these parameters are taken out of the equation when evaluating the accuracy of a given NDI methodology. Once a proper sensitivity (e.g., detectable signal-to-noise ratio) of a given NDI technique is accurately determined, the technique can be used with confidence to reveal various types of porosity defects in the parts 124.

Referring now to FIG. 6, which schematically represents an example of an inspection process 6000. The process 6000 represents portions of or certain operation steps described and illustrated with respect to the method 1000 (FIG. 1) and the method 2000 (FIG. 2). As an example, the process 6000 describes or may be referred to as a method for nondestructively testing parts 124 using the inspection standards 104 of the reference library 102 (e.g., as shown in FIG. 5).

The process 6000 includes a production phase 6002 in which the parts 124 are produced. The process 6000 includes an inspection phase 6004 in which the part 124 is inspected. The process 6000 includes a validation phase 6006 in which the part 124 is validated.

As illustrated, in one or more examples, the part 124 is produced from the powder feedstock 144 using the powder metallurgy process 246. The part 124 includes at least one crack 146 having one or more crack-properties 148 formed during consolidation operations of the powder metallurgy process 246.

The second NDI operation 244 is performed on the part 124. The results of the second NDI operation 244 form the inspection-response 126. The inspection-response 126 is analyzed and compared to the first reference-response 120 and the second reference-response 122. The results of the analysis and comparison (e.g., the inspection operation 272) results in passing or failing of the part 124.

Figure 7:
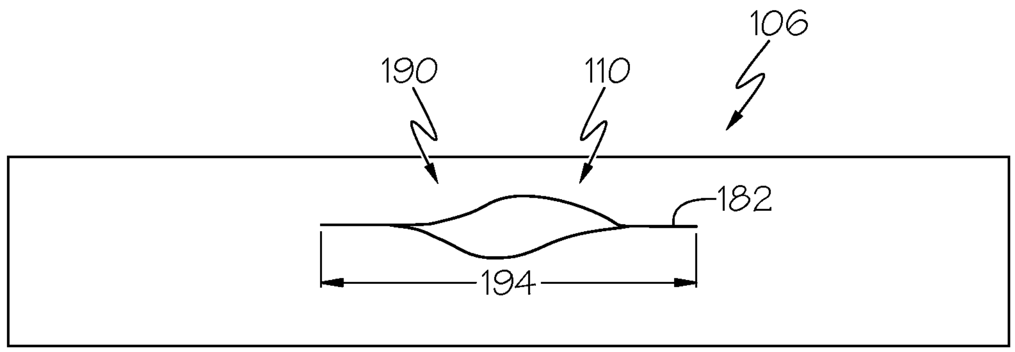
FIG. 7 is a schematic illustration of an example of a first inspection standard.
Figure 7:
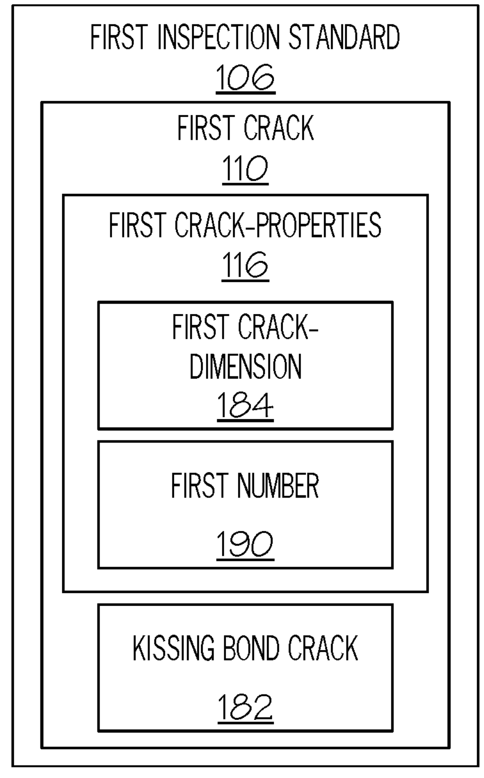
Figure 7:
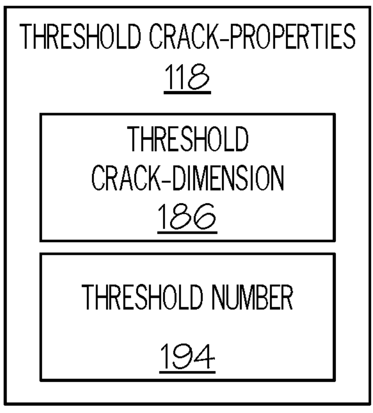

Referring now to FIG. 7, which schematically illustrates an example of the first inspection standard 106. In one or more examples, the first crack 110 includes one or more internal cracks. In one or more examples, the first crack 110 is or includes a kissing bond crack 182.

For the purpose of the present disclosure, a kissing bond crack, also referred to as kissing bond defect, refers to or includes cracks with fracture surface faces that make intimate contact with each other.

As an example, at least a portion of the first crack 110 is a "kissing bond" type crack. However, the first crack 110 may include other types of internal cracking or portions of the first crack 110 may not be of the kissing bond type crack.

While only one first crack 110 is shown by example in FIG. 7, in other examples, the first inspection standard 106 can include any number of first cracks 110.

In one or more examples, the first crack 110 has a first crack-dimension 184. The first crack-dimension 184 is an example of one of the first crack-properties 114. In these examples, one of the threshold crack-properties 118 is a threshold crack-dimension 186.

The threshold crack-dimension 186 refers to a dimension of the crack 146 of a manufactured part (e.g., the part 124) that meets (e.g., is approximately equal to) the design specification of the manufactured part related to crack-dimensions or that is within an acceptable tolerance of the design specification.

In one or more examples, the first crack-dimension 184 of the first crack 110 is less than the threshold crack-dimension 186. As an example, the first crack-dimension 184 of the first crack 110 defines a lower limit or lower tolerance of the threshold crack-dimension 186. For example, the first crack-dimension 184 of the first crack 110 is a minimum crack-dimension allowable for a viable manufactured part.

In one or more examples, the first crack-dimension 184 of the first crack 110 is at least 5% less than the threshold crack-dimension 186. In one or more examples, the first crack-dimension 184 of the first crack 110 is at least 10% less than the threshold crack-dimension 186. In one or more examples, the first crack-dimension 184 of the first crack 110 is at least 25% less than the threshold crack-dimension 186. In one or more examples, the first crack-dimension 184 of the first crack 110 is between approximately at least 5% and at most 25% less than the threshold crack-dimension 186. In one or more examples, the first crack-dimension 184 of the first crack 110 is between approximately at least 5% and at most 10% less than the threshold crack-dimension 186.

Figure 8:
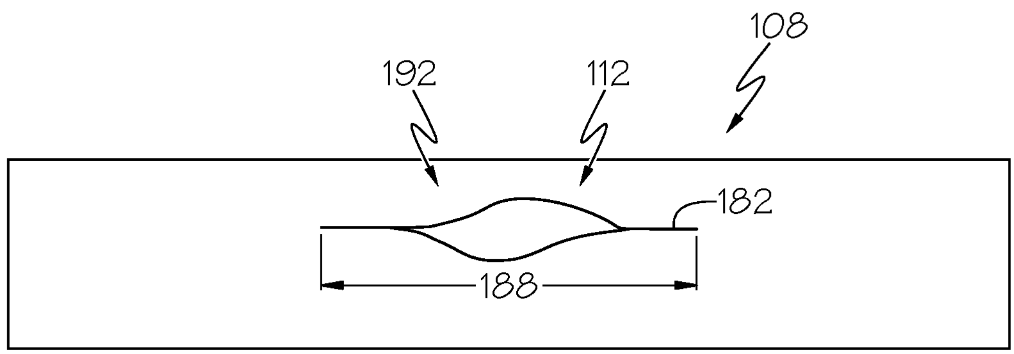
FIG. 8 is a schematic illustration of an example of a second inspection standard.
Figure 8:
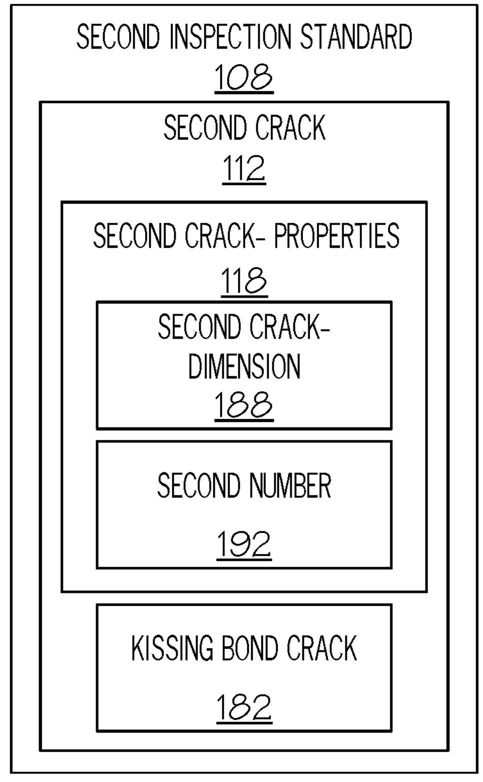
Figure 8:
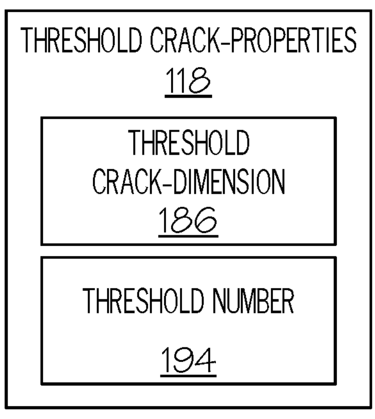

Referring now to FIG. 8, which schematically illustrates an example of the second inspection standard 108. In one or more examples, the second crack 112 includes one or more internal cracks. In one or more examples, the second crack 112 is or includes the kissing bond crack 182.

As an example, at least a portion of the second crack 112 is the "kissing bond" type crack. However, the second crack 112 may include other types of internal cracking or portions of the second crack 112 may not be of the kissing bond type crack.

While only one second crack 112 is shown by example in FIG. 8, in other examples, the second inspection standard 108 can include any number of second cracks 112.

In one or more examples, the second crack 112 has a second crack-dimension 188. The second crack-dimension 188 is an example of one of the second crack-properties 116. In these examples, one of the threshold crack-properties 118 is the threshold crack-dimension 186.

In one or more examples, the second crack-dimension 188 of the second crack 112 is less than the threshold crack-dimension 186. As an example, the second crack-dimension 188 of the second crack 112 defines a lower limit or lower tolerance of the threshold crack-dimension 186. For example, the second crack-dimension 188 of the second crack 112 is a maximum crack-dimension allowable for a viable manufactured part.

In one or more examples, the second crack-dimension 188 of the second crack 112 is at least 5% greater than the threshold crack-dimension 186. In one or more examples, the second crack-dimension 188 of the second crack 112 is at least 10% greater than the threshold crack-dimension 186. In one or more examples, the second crack-dimension 188 of the second crack 112 is at least 25% greater than the threshold crack-dimension 186. In one or more examples, the second crack-dimension 188 of the second crack 112 is between approximately at least 5% and at most 25% greater than the threshold crack-dimension 186. In one or more examples, the second crack-dimension 188 of the second crack 112 is between approximately at least 5% and at most 10% greater than the threshold crack-dimension 186.

Referring again to FIG. 7, in one or more examples, the first inspection standard 106 includes a first number 190 of the first cracks 110. The first number 190 is an example of one of the first crack-properties 114. In these examples, one of the threshold crack-properties 118 is a threshold number 194.

As used herein, a number of cracks refers to a quantity of the cracks 146 or a degree of concentration of the cracks 146 per unit of measurement, such as per unit volume (e.g., three-dimensional number density), per unit area (e.g., two-dimensional number density), or per unit length or width (e.g., one-dimensional number density).

The threshold number 194 refers to a quantity or concentration of the cracks 146 of a manufactured part (e.g., the part 124) that meets (e.g., is approximately equal to) the design specification of the manufactured part related to the number of cracks that is within an acceptable tolerance of the design specification.

In one or more examples, the first number 190 of the first cracks 110 is less than the threshold number 194. As an example, the first number 190 of the first cracks 110 defines a lower limit or lower tolerance of the threshold number 194. For example, the first number 190 of the first cracks 110 is a minimum number of cracks allowable for a viable manufactured part.

Referring again to FIG. 8, in one or more examples, the second inspection standard 108 includes a second number 192 of the second cracks 112. The second number 192 is an example of one of the second crack-properties 116. In these examples, one of the threshold crack-properties 118 is the threshold number 194.

In one or more examples, the second number 192 of the second cracks 112 is greater than the threshold number 194. As an example, the second number 192 of the second cracks 112 defines an upper limit or upper tolerance of the threshold number 194. For example, the second number 192 of the second cracks 112 is a maximum number of cracks allowable for a viable manufactured part.

Other crack-properties of internal cracks may also be used as a reference inspection property and/or as testing threshold property. Generally, the particular crack-property of the crack being used as for reference inspection and/or being tested or otherwise detected relies on an understanding of the requirement specification or an arbitrary series of cracks generated to characterize the threshold of detection and detection sensitivity within a part structure geometry and encompassing the relevant signal to noise ratio.

Figure 9:
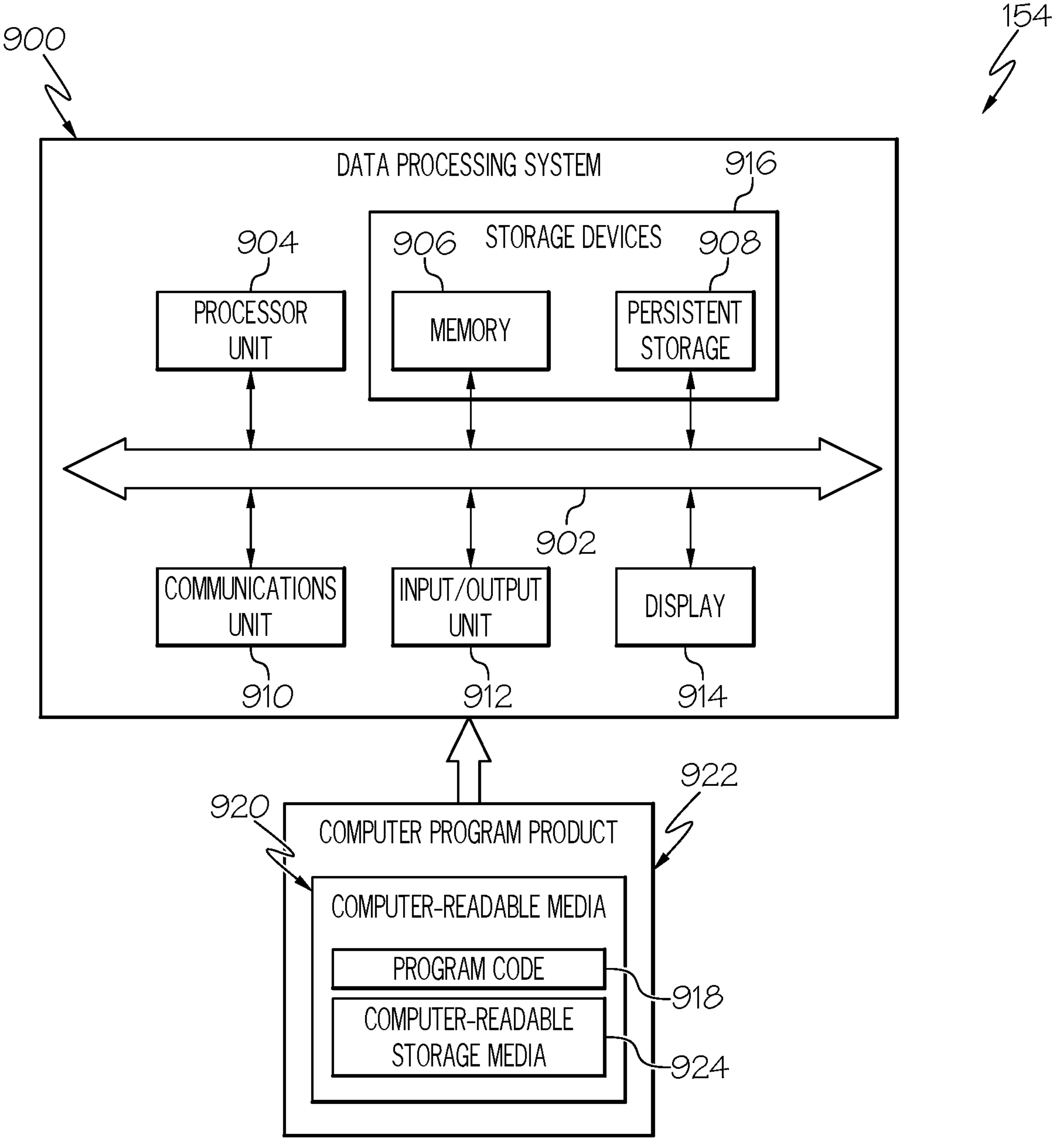
FIG. 9 is a block diagram of an example of a data processing unit.

Referring now to FIG. 9, in one or more examples, the computing device 154 (e.g., shown in FIG. 3) includes the data processing unit 900. In one or more examples, the data processing unit 900 includes a communications framework 902, which provides communications between at least one processor unit 904, one or more storage devices 916, such as memory 906 and/or persistent storage 908, a communications unit 910, an input/output (I/O) unit 912, and a display 914. In this example, the communications framework 902 takes the form of a bus system.

The processor unit 904 serves to execute instructions for software that can be loaded into the memory 906. In one or more examples, the processor unit 904 is a number of processors, a multi-processor core, or some other type of processor, depending on the particular implementation.

The memory 906 and the persistent storage 908 are examples of the storage devices 916. A storage device is any piece of hardware that is capable of storing information, such as, for example, without limitation, at least one of data, program code in functional form, or other suitable information either on a temporary basis, a permanent basis, or both on a temporary basis and a permanent basis. The storage devices 916 may also be referred to as computer readable storage devices in one or more examples. The memory 906 is, for example, a random-access memory or any other suitable volatile or non-volatile storage device. The persistent storage 908 can take various forms, depending on the particular implementation.

For example, the persistent storage 908 contains one or more components or devices. For example, the persistent storage 908 is a hard drive, a solid state hard drive, a flash memory, a rewritable optical disk, a rewritable magnetic tape, or some combination of the above. The media used by the persistent storage 908 also can be removable. For example, a removable hard drive can be used for the persistent storage 908.

The communications unit 910 provides for communications with other data processing systems or devices, such as the first NDI device 150, the second NDI device 152, and the database 156 (e.g., as shown in FIG. 3). In one or more examples, the communications unit 910 is a network interface card.

Input/output unit 912 allows for input and output of data with other devices that can be connected to the data processing unit 900. As an example, the input/output unit 912 provided a connection with a control unit of the first NDI device 150 and/or a control unit of the second NDI device 152. As another example, the input/output unit 912 provides a connection for user input through at least one of a keyboard, a mouse, or some other suitable input device. Further, the input/output unit 912 can send output to a printer. The display 914 provides a mechanism to display information to a user.

Instructions for at least one of the operating system, applications, or programs can be located in the storage devices 916, which are in communication with the processor unit 904 through the communications framework 902. The processes of the various examples and operations described herein can be performed by the processor unit 904 using computer-implemented instructions, which can be located in a memory, such as the memory 906.

The instructions are referred to as program code, computer usable program code, or computer readable program code that can be read and executed by a processor of the processor unit 904. The program code in the different examples can be embodied on different physical or computer readable storage media, such as the memory 906 or the persistent storage 908.

In one or more examples, program code 918 is located in a functional form on computer readable media 920 that is selectively removable and can be loaded onto or transferred to the data processing unit 900 for execution by the processor unit 904. In one or more examples, the program code 918 and computer readable media 920 form a computer program product 922. In one or more examples, the computer readable media 920 is computer readable storage media 924.

In one or more examples, the computer readable storage media 924 is a physical or tangible storage device used to store the program code 918 rather than a medium that propagates or transmits the program code 918.

Alternatively, the program code 918 can be transferred to the data processing unit 900 using a computer readable signal media. The computer readable signal media can be, for example, a propagated data signal containing the program code 918. For example, the computer readable signal media can be at least one of an electromagnetic signal, an optical signal, or any other suitable type of signal. These signals can be transmitted over at least one of communications links, such as wireless communications links, optical fiber cable, coaxial cable, a wire, or any other suitable type of communications link.

The different components illustrated for data processing unit 900 are not meant to provide architectural limitations to the manner in which different examples can be implemented. The different examples can be implemented in a data processing system including components in addition to or in place of those illustrated for the data processing unit 900. Other components shown in FIG. 9 can be varied from the examples shown. The different examples can be implemented using any hardware device or system capable of running the program code 918.

Additionally, various components of the computing device 154 and/or the data processing unit 900 may be described as modules. For the purpose of the present disclosure, the term "module" includes hardware, software or a combination of hardware and software. As an example, a module can include one or more circuits configured to perform or execute the described functions or operations of the executed processes described herein (e.g., the method 1000, the method 2000, the process 5000, and the process 6000). As another example, a module includes a processor, a storage device (e.g., a memory), and computer-readable storage medium having instructions that, when executed by the processor causes the processor to perform or execute the described functions and operations. In one or more examples, a module takes the form of the program code 918 and the computer readable media 920 together forming the computer program product 922.

Figure 11:
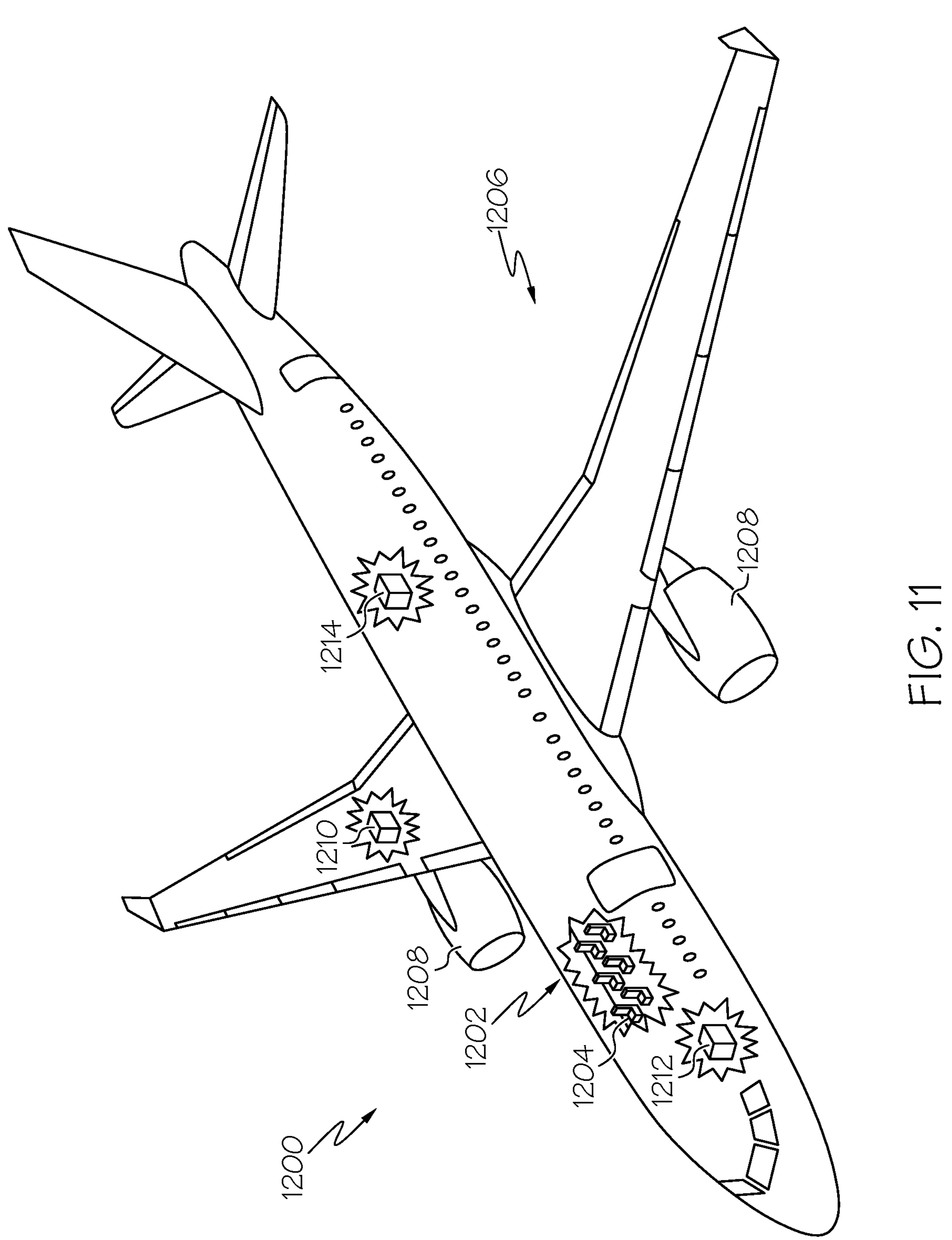
FIG. 11 is a schematic illustration of an example of an aircraft.

Referring now to FIGS. 10 and 11, examples of the system 100, the method 1000, and the method 2000, described herein, may be related to, or used in the context of, an aircraft manufacturing and service method 1100, as shown in the flow diagram of FIG. 10 and an aircraft 1200, as schematically illustrated in FIG. 11. For example, the aircraft 1200 and/or the aircraft production and service method 1100 may utilize powder metal parts (e.g., parts 124) manufactured and inspected using the system 100 and/or according to the method 1000 and/or the method 2000.

Referring to FIG. 11, which illustrates an example of the aircraft 1200. The aircraft 1200 also includes an airframe 1202 having an interior 1204. The aircraft 1200 includes a plurality of onboard systems 1206 (e.g., high-level systems). Examples of the onboard systems 1206 of the aircraft 1200 include propulsion systems 1208, hydraulic systems 1210, electrical systems 1212, and environmental systems 1214. In other examples, the onboard systems 1206 also includes one or more control systems coupled to an airframe 1202 of the aircraft 1200, such as for example, flaps, spoilers, ailerons, slats, rudders, elevators, and trim tabs. In yet other examples, the onboard systems 1206 also includes one or more other systems, such as, but not limited to, communications systems, avionics systems, software distribution systems, network communications systems, passenger information/entertainment systems, guidance systems, radar systems, weapons systems, and the like.

Referring to FIG. 10, during pre-production of the aircraft 1200, the method 1100 includes specification and design of the aircraft 1200 (block 1102) and material procurement (block 1104). During production of the aircraft 1200, component and subassembly manufacturing (block 1106) and system integration (block 1108) of the aircraft 1200 take place. Thereafter, the aircraft 1200 goes through certification and delivery (block 1110) to be placed in service (block 1112). Routine maintenance and service (block 1114) includes modification, reconfiguration, refurbishment, etc. of one or more systems of the aircraft 1200.

Each of the processes of the method 1100 illustrated in FIG. 10 may be performed or carried out by a system integrator, a third party, and/or an operator (e.g., a customer). For the purposes of this description, a system integrator may include, without limitation, any number of spacecraft manufacturers and major-system subcontractors; a third party may include, without limitation, any number of vendors, subcontractors, and suppliers; and an operator may be an airline, leasing company, military entity, service organization, and so on.

Examples of the system 100, the method 1000, and the method 2000 shown and described herein, may be employed during any one or more of the stages of the manufacturing and service method 1100 shown in the flow diagram illustrated by FIG. 10. In an example, manufacturing and non-destructive testing of powder metal parts (e.g., the parts 124)

using the system 100 or according to the method 1000 or the method 2000 may form a portion of component and subassembly manufacturing (block 1106) and/or system integration (block 1108). Further, manufacturing and nondestructive testing of powder metal parts (e.g., the parts 124) using the system 100 or according to the method 1000 or the method 2000 may be implemented in a manner similar to components or subassemblies prepared while the aircraft 1200 is in service (block 1100). Also, powder metal parts (e.g., the parts 124) manufactured and nondestructive tested using the system 100 or according to the method 1000 or the method 2000 may be utilized during system integration (block 1108) and certification and delivery (block 1110). Similarly, powder metal parts (e.g., the parts 124) manufactured and nondestructive tested using the system 100 or according to the method 1000 or the method 2000 may be utilized, for example and without limitation, while the aircraft 1200 is in service (block 1112) and during maintenance and service (block 1114).

The preceding detailed description refers to the accompanying drawings, which illustrate specific examples described by the present disclosure. Other examples having different structures and operations do not depart from the scope of the present disclosure. Like reference numerals may refer to the same feature, element, or component in the different drawings. Throughout the present disclosure, any one of a plurality of items may be referred to individually as the item and a plurality of items may be referred to collectively as the items and may be referred to with like reference numerals. Moreover, as used herein, a feature, element, component, or step preceded with the word "a" or "an" should be understood as not excluding a plurality of features, elements, components or steps, unless such exclusion is explicitly recited.

Illustrative, non-exhaustive examples, which may be, but are not necessarily, claimed, of the subject matter according to the present disclosure are provided above. Reference herein to "example" means that one or more feature, structure, element, component, characteristic, and/or operational step described in connection with the example is included in at least one aspect, embodiment, and/or implementation of the subject matter according to the present disclosure. Thus, the phrases "an example," "another example," "one or more examples," and similar language throughout the present disclosure may, but do not necessarily, refer to the same example. Further, the subject matter characterizing any one example may, but does not necessarily, include the subject matter characterizing any other example. Moreover, the subject matter characterizing any one example may be, but is not necessarily, combined with the subject matter characterizing any other example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, device, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware that enable the system, apparatus, structure, article, element, component, or hardware to perform the specified function without further modification. For purposes of this disclosure, a system, apparatus, device, structure, article, element, component, or hardware described as being "configured to" perform a particular function may additionally or alternatively be described as being "adapted to" and/or as being "operative to" perform that function.

Unless otherwise indicated, the terms "first," "second," "third," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations. As used herein, the term "and/or" and the "/" symbol includes any and all combinations of one or more of the associated listed items.

For the purpose of this disclosure, the terms "coupled," "coupling," and similar terms refer to two or more elements that are joined, linked, fastened, attached, connected, put in communication, or otherwise associated (e.g., mechanically, electrically, fluidly, optically, electromagnetically) with one another. In various examples, the elements may be associated directly or indirectly. As an example, element A may be directly associated with element B. As another example, element A may be indirectly associated with element B, for example, via another element C. It will be understood that not all associations among the various disclosed elements are necessarily represented. Accordingly, couplings other than those depicted in the figures may also exist.

As used herein, the term "approximately" refers to or represent a condition that is close to, but not exactly, the stated condition that still performs the desired function or achieves the desired result. As an example, the term "approximately" refers to a condition that is within an acceptable predetermined tolerance or accuracy, such as to a condition that is within 10% of the stated condition. However, the term "approximately" does not exclude a condition that is exactly the stated condition. As used herein, the term "substantially" refers to a condition that is essentially the stated condition that performs the desired function or achieves the desired result.

FIGS. 3-9 and 11, referred to above, may represent functional elements, features, or components thereof and do not necessarily imply any particular structure. Accordingly, modifications, additions and/or omissions may be made to the illustrated structure. Additionally, those skilled in the art will appreciate that not all elements, features, and/or components described and illustrated in FIGS. 3-9 and 11, referred to above, need be included in every example and not all elements, features, and/or components described herein are necessarily depicted in each illustrative example. Accordingly, some of the elements, features, and/or components described and illustrated in FIGS. 3-9 and 11 may be combined in various ways without the need to include other features described and illustrated in FIGS. 3-9 and 11, other drawing figures, and/or the accompanying disclosure, even though such combination or combinations are not explicitly illustrated herein. Similarly, additional features not limited to the examples presented, may be combined with some or all of the features shown and described herein. Unless otherwise explicitly stated, the schematic illustrations of the examples depicted in FIGS. 3-9 and 11, referred to above, are not meant to imply structural limitations with respect to the illustrative example. Rather, although one illustrative structure is indicated, it is to be understood that the structure may be modified when appropriate. Accordingly, modifications, additions and/or omissions may be made to the illustrated structure. Furthermore, elements, features, and/or components that serve a similar, or at least substantially similar, purpose are labeled with like numbers in each of FIGS. 3-9 and 11, and such elements, features, and/or components may not be discussed in detail herein with reference to each of FIGS. 3-9 and 11. Similarly, all elements, features, and/or components may not be labeled in each of FIGS. 3-9 and 11, but reference numerals associated therewith may be utilized herein for consistency.

In FIGS. 1, 2 and 10, referred to above, the blocks may represent operations, steps, and/or portions thereof and lines connecting the various blocks do not imply any particular order or dependency of the operations or portions thereof. It will be understood that not all dependencies among the various disclosed operations are necessarily represented. FIGS. 1, 2 and 10 and the accompanying disclosure describing the operations of the disclosed methods set forth herein should not be interpreted as necessarily determining a sequence in which the operations are to be performed. Rather, although one illustrative order is indicated, it is to be understood that the sequence of the operations may be modified when appropriate. Accordingly, modifications, additions and/or omissions may be made to the operations illustrated and certain operations may be performed in a different order or simultaneously. Additionally, those skilled in the art will appreciate that not all operations described need be performed.

Further, references throughout the present specification to features, advantages, or similar language used herein do not imply that all of the features and advantages that may be realized with the examples disclosed herein should be, or are in, any single example. Rather, language referring to the features and advantages is understood to mean that a specific feature, advantage, or characteristic described in connection with an example is included in at least one example. Thus, discussion of features, advantages, and similar language used throughout the present disclosure may, but do not necessarily, refer to the same example.

The described features, advantages, and characteristics of one example may be combined in any suitable manner in one or more other examples. One skilled in the relevant art will recognize that the examples described herein may be practiced without one or more of the specific features or advantages of a particular example. In other instances, additional features and advantages may be recognized in certain examples that may not be present in all examples. Furthermore, although various examples of the system 100, the method 1000, and the method 2000, along with associated processes 5000 and 6000, have been shown and described, modifications may occur to those skilled in the art upon reading the specification. The present application includes such modifications and is limited only by the scope of the claims.

What is claimed is:

1. A method, comprising steps of:

forming a first inspection standard using a metal injection molding process;

forming a second inspection standard using the metal injection molding process;

creating a reference library of physical artifacts comprising the first inspection standard and the second inspection standard; and qualifying a part formed using a powder metallurgy process using the first inspection standard and the second inspection standard based on a comparison of responses from nondestructive inspection, wherein:

the first inspection standard comprises a first crack that is intentionally induced by introducing at least one of a thermal stress or a thermal shock during a sintering operation of the metal injection molding process;

the second inspection standard comprises a second crack that is intentionally induced by introducing at least one of the thermal stress or the thermal shock during the sintering operation of the metal injection molding process;

at least one of the thermal stress or the thermal shock introduced during the sintering operation for the first inspection standard is selected to be different than at least one of the thermal stress or the thermal shock introduced during the sintering operation for the second inspection standard; and the first crack and the second crack are different.

2. The method of claim 1, wherein:

the step of forming the first inspection standard comprises increasing a sintering temperature during the sintering operation at a first heating rate that is greater than an operational heating rate of the sintering operation to introduce the thermal stress; and the step of forming the second inspection standard comprises increasing the sintering temperature during the sintering operation at a second heating rate that is greater than the first heating rate to introduce the thermal stress.

3. The method of claim 1, wherein:

the step of forming the first inspection standard comprises decreasing a sintering temperature during the sintering operation at a first cooling rate that is greater than an operational cooling rate of the sintering operation to introduce the thermal stress; and the step of forming the second inspection standard comprises decreasing the sintering temperature during the sintering operation at a second cooling rate that is greater than the first cooling rate to introduce the thermal stress.

4. The method of claim 1, wherein:

the step of forming the first inspection standard comprises cycling between a first sintering temperature and a second sintering temperature during the sintering operation a first number of cycles to introduce the thermal stress; and the step of forming the second inspection standard comprises cycling between the first sintering temperature and the second sintering temperature during the sintering operation at a second number of the cycles, which different than the first number of the cycles, to introduce the thermal stress.

5. The method of claim 1, wherein:

the step of forming the first inspection standard comprises cycling between a first minimum temperature and a first maximum temperature during the sintering operation to introduce the thermal shock; and the step of forming the second inspection standard comprises cycling between a second minimum temperature and a second maximum temperature during the sintering operation to introduce the thermal shock.

6. The method of claim 1, wherein:

the first crack comprises a first crack-property;

the second crack comprises a second crack-property; and the first crack-property and the second crack-property are different.

7. The method of claim 6, wherein:

the first crack-property is below a threshold crack-property; and the second crack-property is above the threshold crack-property.

8. The method of claim 6, further comprising:

performing a first nondestructive inspection operation on the first inspection standard to verify that the first crack-property is below a threshold crack-property; and performing the first nondestructive inspection operation on the second inspection standard to verify that the second crack-property is above the threshold crack-property.

9. The method of claim 8, further comprising:

performing a second nondestructive inspection operation on the first inspection standard;

recording a first reference-response to the second nondestructive inspection operation associated with the first inspection standard;

performing the second nondestructive inspection operation on the second inspection standard; and recording a second reference-response to the second nondestructive inspection operation associated with the second inspection standard.

10. The method of claim 9, wherein:

the first nondestructive inspection operation is a visual nondestructive inspection methodology; and the second nondestructive inspection operation is a non-visual nondestructive inspection methodology.

11. The method of claim 9, further comprising:

forming a part using a powder metallurgy process;

performing the second nondestructive inspection operation on the part;

recording an inspection-response to the second nondestructive inspection operation associated with the part; and comparing the inspection-response to the first reference-response and the second reference-response.

12. A method, comprising steps of:

forming a plurality of inspection standards using a metal injection molding process;

during the metal injection molding process, intentionally introducing at least one of a thermal shock or a thermal stress during a sintering operation of the metal injection molding process to induce a crack in each one of the inspection standards;

performing a first nondestructive inspection operation on each one of the inspection standards to determine a crack-property of the crack of each one of the inspection standards;

selecting a first one of the inspection standards in which the crack-property of the crack is below a predetermined threshold crack-property for use as a lower boundary qualification standard; and selecting a second one of the inspection standards in which the crack-property of the crack is above the threshold crack-property for use as an upper boundary qualification standard.

13. The method of claim 12, further comprising creating a reference library of physical artifacts comprising at least the first one of the inspection standards and the second one of the inspection standards.

14. The method of claim 12, wherein the step of introducing the thermal stress comprises at least one of:

increasing a sintering temperature during the sintering operation at a heating rate that is greater than an operational heating rate of the sintering operation; or decreasing the sintering temperature during the sintering operation at a cooling rate that is greater than an operational cooling rate of the sintering operation.

15. The method of claim 12, wherein the step of introducing the thermal stress comprises cycling between different temperatures during interruption of the sintering operation a number of cycles.

16. The method of claim 12, wherein the step of introducing the thermal shock comprises cycling between a minimum temperature and a maximum temperature at a rate higher than a sintering temperature rate during interruption of the sintering operation.

17. The method of claim 12, further comprising:

performing a non-visual nondestructive inspection operation on the first one of the inspection standards;

recording a first reference-response to the non-visual nondestructive inspection operation associated with the first one of the inspection standards and representing a lower boundary qualification;

performing the non-visual nondestructive inspection operation on the second one of the inspection standards; and recording a second reference-response to the non-visual nondestructive inspection operation associated with the second one of the inspection standards and representing an upper boundary qualification.

18. The method of claim 17, further comprising:

forming a part using a powder metallurgy process;

performing the non-visual nondestructive inspection operation on the part;

recording an inspection-response to the non-visual nondestructive inspection operation associated with the part;

comparing the inspection-response to the first reference-response and the second reference-response; and qualifying the part based on a comparison of the inspection-response to the first reference-response and the second reference-response.

19. A system, comprising:

a reference library of physical artifacts comprising at least a first inspection standard and a second inspection standard formed by a metal injection molding process, wherein:

the first inspection standard comprises a first crack that is intentionally induced by introducing at least one of a thermal shock or a thermal stress during a sintering operation of the metal injection molding process;

the second inspection standard comprises a second crack that is intentionally induced by introducing at least one of the thermal shock or the thermal stress during the sintering operation of the metal injection molding process;

the first crack comprises a first crack-property that is below a threshold crack-property; and the second crack comprises a second crack-property that is above the threshold crack-property; and a first nondestructive inspection device configured to:

inspect the first inspection standard and the second inspection standard; and qualitatively verify that the first crack-property is below the threshold crack-property and that the second crack-property is above the threshold crack-property;

a second nondestructive inspection device configured to:

inspect the first inspection standard and the second inspection standard;

produce a first reference-response associated with the first crack-property of the first inspection standard; and produce a second reference-response associated with the second crack-property of the second inspection standard; and a computing device configured to:

store the first reference-response and the second reference-response; and qualify a part formed using a powder metallurgy process using the first reference-response and the second reference-response based on a comparison of a response from nondestructive inspection of the part.

20. The system of claim 19, wherein:

the second nondestructive inspection device is configured to:

inspect a part formed by a powder metallurgy process; and produce an inspection-response associated a crack-property of the part; and the computing device is configured to compare the inspection-response to the first reference-response and the second reference-response.

* * * * *